(12) United States Patent
Benner

(10) Patent No.: US 9,297,041 B1
(45) Date of Patent: Mar. 29, 2016

(54) INEXPENSIVE AUTONOMOUS ASSEMBLY OF ULTRA-LARGE (UL) DNA CONSTRUCTS

(71) Applicant: Steven Albert Benner, Gainesville, FL (US)

(72) Inventor: Steven Albert Benner, Gainesville, FL (US)

( * ) Notice: Subject to any disclaimer, the term of this patent is extended or adjusted under 35 U.S.C. 154(b) by 65 days.

(21) Appl. No.: 14/048,671

(22) Filed: Oct. 8, 2013

Related U.S. Application Data

(63) Continuation-in-part of application No. 13/936,309, filed on Jul. 8, 2013, now abandoned.

(60) Provisional application No. 61/669,295, filed on Jul. 9, 2012.

(51) Int. Cl.
*C12Q 1/68* (2006.01)
*C12P 19/34* (2006.01)

(52) U.S. Cl.
CPC .............. *C12Q 1/6862* (2013.01); *C12P 19/34* (2013.01); *C12Q 2521/501* (2013.01); *C12Q 2525/117* (2013.01)

(58) Field of Classification Search
CPC ........... C12Q 1/6862; C12Q 2521/501; C12Q 2525/117
USPC ......................................... 435/6.1, 91.1, 91.2
See application file for complete search history.

(56) References Cited

U.S. PATENT DOCUMENTS 7,741,294 B1    6/2010 Benner

OTHER PUBLICATIONS

U.S. Appl. No. 12/653,613, filed Dec. 16, 2009, Steven A. Benner.

*Primary Examiner* — Jezia Riley

(57) ABSTRACT

This invention provides processes to assemble many (greater than 20) partially overlapping single stranded DNA molecules (fragments) having preselected sequences, followed by extension of those strands that hybridize at terminal overlap regions, and ligation of the extend products, creating a double-stranded DNA assembly. These processes use non-standard nucleotides carrying heterocyclic nucleobase analogs that implement non-standard hydrogen bonding patterns; these allow controlled annealing of the single stranded fragments via Watson-Crick rules, with less or no interference from a range of non-Watson Crick interactions, hairpin formations, or off-target hybridization displayed by standard nucleobases. This process includes an optional conversion step that replaces non-standard nucleobase pairs with standard nucleobase pairs, generating large synthetic DNA (LS-DNA) molecules containing only natural nucleotides. As useful application, this invention allows the assembly of genes encoding whole proteins (typically 1000-3000 nucleotide pairs) from a collection of single stranded DNA fragments at reduced cost and effort.

9 Claims, 12 Drawing Sheets

Figure 1:
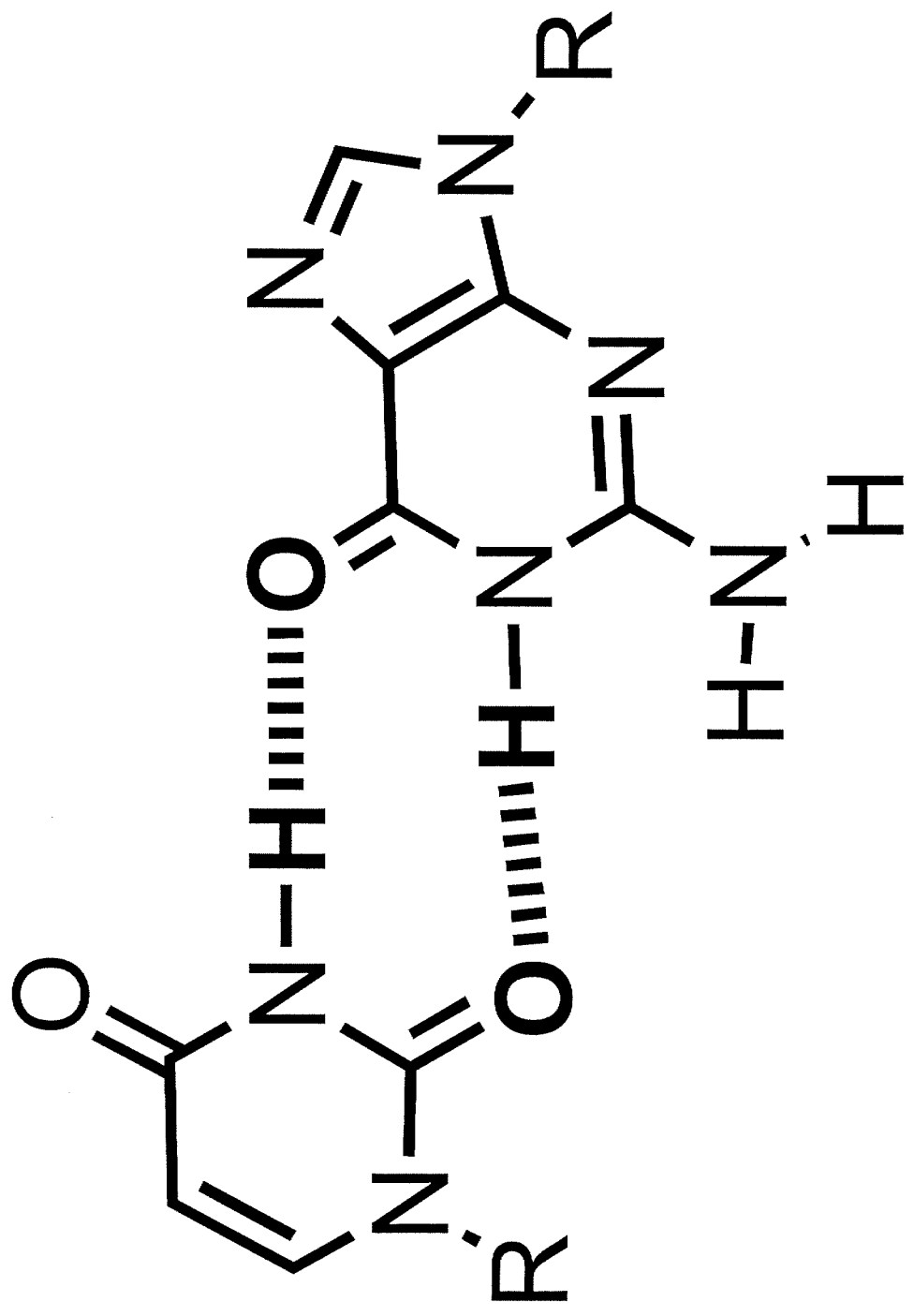

G-quartet
non-canonical, very stable fold major groove "Hoogsteen" binding

SEQUENCE LISTING

<160> NUMBER OF SEQ ID NOS: 29

<210> SEQ ID NO 1
<211> LENGTH: 66
<212> TYPE: DNA
<213> ORGANISM: Artificial Sequence

```
<220> FEATURE:
<223> OTHER INFORMATION: Synthetic

<400> SEQUENCE: 1
caccatgagc catattcaac gggaaacgtc gaggccgcga ttaaattcca acatggasgc      60 sgastt                                                                66

<210> SEQ ID NO 2
<211> LENGTH: 52
<212> TYPE: DNA
<213> ORGANISM: Artificial Sequence
<220> FEATURE:
<223> OTHER INFORMATION: Synthetic

<400> SEQUENCE: 2
sgastgcccg acbttatcgc gagcccattt atacccatat aabtcbgcbt cc             52

<210> SEQ ID NO 3
<211> LENGTH: 58
<212> TYPE: DNA
<213> ORGANISM: Artificial Sequence
<220> FEATURE:
<223> OTHER INFORMATION: Synthetic

<400> SEQUENCE: 3
sgtcgggcab tcbggtgcga caatctatcg cttgtatggg aagcccgasg cgccbgag       58

<210> SEQ ID NO 4
<211> LENGTH: 53
<212> TYPE: DNA
<213> ORGANISM: Artificial Sequence
<220> FEATURE:
<223> OTHER INFORMATION: Synthetic

<400> SEQUENCE: 4
bacbtcbttg gcbacgctac ctttgccatg tttcagaaac aactcsggcg cbt            53

<210> SEQ ID NO 5
<211> LENGTH: 62
<212> TYPE: DNA
<213> ORGANISM: Artificial Sequence
<220> FEATURE:
<223> OTHER INFORMATION: Synthetic

<400> SEQUENCE: 5
sgccaasgas gtsacagatg agatggtcag actaaactgg ctgacggabt ttatgccsct     60 sc                                                                    62

<210> SEQ ID NO 6
<211> LENGTH: 49
<212> TYPE: DNA
<213> ORGANISM: Artificial Sequence
<220> FEATURE:
<223> OTHER INFORMATION: Synthetic

<400> SEQUENCE: 6
tcbtcbggbg tbcggataaa atgcttgatg gtcggbagbg gcataaast                 49

<210> SEQ ID NO 7
<211> LENGTH: 54
<212> TYPE: DNA
<213> ORGANISM: Artificial Sequence
<220> FEATURE:
<223> OTHER INFORMATION: Synthetic
```

<400> SEQUENCE: 7
sacsccsgas gatgcatggt tactcaccac tgcgatcccc ggbaaaacbg cbtt    54

<210> SEQ ID NO 8
<211> LENGTH: 57
<212> TYPE: DNA
<213> ORGANISM: Artificial Sequence
<220> FEATURE:
<223> OTHER INFORMATION: Synthetic

<400> SEQUENCE: 8
cbacaatbtt stcbcctgaa tcaggatatt cttctaatac ctggaasgcs gttttsc    57

<210> SEQ ID NO 9
<211> LENGTH: 59
<212> TYPE: DNA
<213> ORGANISM: Artificial Sequence
<220> FEATURE:
<223> OTHER INFORMATION: Synthetic

<400> SEQUENCE: 9
sgabaasatt gtsgatgcgc tggcagtgtt cctgcgccgg ttgcastcga ttcctgtst    59

<210> SEQ ID NO 10
<211> LENGTH: 57
<212> TYPE: DNA
<213> ORGANISM: Artificial Sequence
<220> FEATURE:
<223> OTHER INFORMATION: Synthetic

<400> SEQUENCE: 10
gbgcgagbcg aaatacgcga tcgctgttaa aaggacaatt acabacagga atcgabt    57

<210> SEQ ID NO 11
<211> LENGTH: 47
<212> TYPE: DNA
<213> ORGANISM: Artificial Sequence
<220> FEATURE:
<223> OTHER INFORMATION: Synthetic

<400> SEQUENCE: 11
tcgsctcgcs caggcgcaat cacgaatgaa taacggsttg gtsgasg    47

<210> SEQ ID NO 12
<211> LENGTH: 57
<212> TYPE: DNA
<213> ORGANISM: Artificial Sequence
<220> FEATURE:
<223> OTHER INFORMATION: Synthetic

<400> SEQUENCE: 12
cstgstcbac bggccagcca ttacgctcgt catcaaaatc actcgcbtcb accaabc    57

<210> SEQ ID NO 13
<211> LENGTH: 41
<212> TYPE: DNA
<213> ORGANISM: Artificial Sequence
<220> FEATURE:
<223> OTHER INFORMATION: Synthetic

<400> SEQUENCE: 13
sgtsgabcab gtctggaaag aaatgcasaa bctsttgccb t    41

<210> SEQ ID NO 14
<211> LENGTH: 59

<212> TYPE: DNA
<213> ORGANISM: Artificial Sequence
<220> FEATURE:
<223> OTHER INFORMATION: Synthetic

<400> SEQUENCE: 14
btcbagsgag aabtcaccat gagtgacgac tgaatccggt gagaasggca abagsttbt      59

<210> SEQ ID NO 15
<211> LENGTH: 67
<212> TYPE: DNA
<213> ORGANISM: Artificial Sequence
<220> FEATURE:
<223> OTHER INFORMATION: Synthetic

<400> SEQUENCE: 15
asttctcbct sgasaacctt atttttgacg aggggaaatt aataggttgt attgasgttg      60 gacgbgt                                                               67

<210> SEQ ID NO 16
<211> LENGTH: 44
<212> TYPE: DNA
<213> ORGANISM: Artificial Sequence
<220> FEATURE:
<223> OTHER INFORMATION: Synthetic

<400> SEQUENCE: 16
cbagbtcctg gtascggtct gcgattccga cscgtccaac btca                      44

<210> SEQ ID NO 17
<211> LENGTH: 62
<212> TYPE: DNA
<213> ORGANISM: Artificial Sequence
<220> FEATURE:
<223> OTHER INFORMATION: Synthetic

<400> SEQUENCE: 17
btaccaggas ctsgccatcc tatggaactg cctcggtgag ttttctccst cbttacagaa      60 bc                                                                    62

<210> SEQ ID NO 18
<211> LENGTH: 59
<212> TYPE: DNA
<213> ORGANISM: Artificial Sequence
<220> FEATURE:
<223> OTHER INFORMATION: Synthetic

<400> SEQUENCE: 18
sttbttcatb tcbggattat caataccata tttttgaaaa agccgsttct gtaasgabg       59

<210> SEQ ID NO 19
<211> LENGTH: 68
<212> TYPE: DNA
<213> ORGANISM: Artificial Sequence
<220> FEATURE:
<223> OTHER INFORMATION: Synthetic

<400> SEQUENCE: 19
csgasatgaa saabttgcag tttcatttga tgctcgatga gttttctaa caggatccgc       60 bcgbcsag                                                              68

<210> SEQ ID NO 20
<211> LENGTH: 42
<212> TYPE: DNA

<213> ORGANISM: Artificial Sequence
<220> FEATURE:
<223> OTHER INFORMATION: Synthetic

<400> SEQUENCE: 20

```
ctagsggscg btcsgtccgt cctgtcagct gctbgscgsg cg                          42
```

<210> SEQ ID NO 21
<211> LENGTH: 22
<212> TYPE: DNA
<213> ORGANISM: Artificial Sequence
<220> FEATURE:
<223> OTHER INFORMATION: Synthetic

<400> SEQUENCE: 21

```
caccatgagc catattcaac gg                                               22
```

<210> SEQ ID NO 22
<211> LENGTH: 18
<212> TYPE: DNA
<213> ORGANISM: Artificial Sequence
<220> FEATURE:
<223> OTHER INFORMATION: Synthetic

<400> SEQUENCE: 22

```
gtccgtcctg tcagctgc                                                    18
```

<210> SEQ ID NO 23
<211> LENGTH: 863
<212> TYPE: DNA
<213> ORGANISM: Artificial Sequence
<220> FEATURE:
<223> OTHER INFORMATION: Synthetic

<400> SEQUENCE: 23

```
ctagtggscg btctgsccgt cctgtcagct gctbgscgsg cggatcctgt tagaaaaact      60
catcgagcat caaatgaaac tgcaasttbt tcatbtcbgg attatcaata ccatattttt     120
gaaaaagccg sttctgtaas gabggagaaa actcaccgag gcagttccat aggatggcba    180
gbtcctggta scggtctgcg attccgacsc gsccbacbtc aatacaacct attaatttcc    240
cctcgtcaaa aataaggttb tcbagsgaga abtcaccatg agtgacgact gaatccggtg    300
agaasggcaa bagsttbtgc atttctttcc agacstgstc bacbggccag ccattacgct    360
cgtcatcaaa atcactcgcb tcbaccaabc cgttattcat tcgtgattgc gcctgbgcga    420
gbcgaaatac gcgatcgctg ttaaaaggac aattacbaac bggaatcgab tgcaaccggc    480
gcaggaacac tgccagcgca tcbacaatbt tstcbcctga atcaggatat tcttctaata    540
cctggaasgc sgtsttsccg gggatcgcag tggtgagtaa ccatgcatcb tcbggbgtbc    600
ggataaaatg cttgatggtc ggbagbggca taaastccgt cagccagttt agtctgacca    660
tctcatctgt bacbtcbttg gcabcgctac ctttgccatg tttcagaaac aactcsggcg    720
cbtcgggctt cccatacaag cgatagattg tcgcaccsga stgcccgacb ttatcgcgag    780
cccatttata cccatataab tcbgcbtcca tgttggaatt taatcgcggc ctcgacgttt    840
cccgttgaat atggctcatg gtg                                             863
```

<210> SEQ ID NO 24
<211> LENGTH: 810
<212> TYPE: DNA
<213> ORGANISM: Artificial Sequence
<220> FEATURE:
<223> OTHER INFORMATION: Synthetic

<400> SEQUENCE: 24

```
ttagaaaaac tcatcgagca tcaaatgaaa ctgcaattta ttcatatcag gattatcaat    60
accatatttt tgaaaaagcc gtttctgtaa tgaaggagaa aactcaccga ggcagttcca   120
taggatggca agatcctggt atcggtctgc gattccgact cgtccaacat caatacaacc   180
tattaatttc ccctcgtcaa aaataaggtt atcaagtgag aaatcaccat gagtgacgac   240
tgaatccggt gagaatggca aaagtttatg catttctttc cagacttgtt caacaggcca   300
gccattacgc tcgtcatcaa aatcactcgc atcaaccaaa ccgttattca ttcgtgattg   360
cgcctgagcg agacgaaata cgcgatcgct gttaaaagga caattacaaa caggaatcga   420
atgcaaccgg cgcaggaaca ctgccagcgc atcaacaata ttttcacctg aatcaggata   480
ttcttctaat acctggaatg ctgttttttcc ggggatcgca gtggtgagta accatgcatc   540
atcaggagta cggataaaat gcttgatggt cggaagaggc ataaattccg tcagccagtt   600
tagtctgacc atctcatctg taacatcatt ggcaacgcta cctttgccat gtttcagaaa   660
caactctggc gcatcgggct tcccatacaa gcgatagatt gtcgcacctg attgcccgac   720
attatcgcga gcccatttat acccatataa atcagcatcc atgttggaat ttaatcgcgg   780
cctcgacgtt tcccgttgaa tatggctcat                                    810
```

<210> SEQ ID NO 25
<211> LENGTH: 849
<212> TYPE: DNA
<213> ORGANISM: Artificial Sequence
<220> FEATURE:
<223> OTHER INFORMATION: Synthetic

<400> SEQUENCE: 25

```
gtccgacctg tcagctgcta gtcgtgcgga tcctgtcaga aaaactcatc gagcatcaaa    60
tgaaactgca atttgttcat atccggatta tcaataccat attttttgaaa aagccgtttc   120
tgtaatgaag gacaaaactc accgaggcag ttccatagga tggcaagatc ctggtatcgg   180
tctgcgattc cgactcgtcc aacatcaata aacctatta atttcccctc gtcaaaaata   240
aggttatcaa gtgagaaatc accatgagtg acgactgaat ccggtgagaa tggcaaaagt   300
ttatgcattt ctttccagac ttgttcaaca ggccagccat tacgctcgtc atcaaaatca   360
ctcgcatcaa ccaacccgtt attcattcgt gattgcgcct gagcgagacg aaatacgcga   420
tcgctgttaa aaggacaatt acaaacagga atcgaatgca accggcgcag gaacactgcc   480
agcgcatcaa caatattttc acctgaatca ggatattctt ctaatacctg gaatgctgtt   540
tttccgggga tcgcagtggt gagtaaccat gcatcatcag gagtacggat aaaatgcttg   600
atggtcggaa gaggcataaa ttccgtcagc cagtttagtc tgaccatctc atctgtaaca   660
tcattggcaa cgctaccttt gccatgtttc agaaacaact ctggcgcatc gggcttccca   720
tacaagcgat agattgtcgc acctgattgc ccgacattat cgcgagccca tttataccca   780
tataaatcag catccatgtt ggaatttaat cgcggcctcg acgtttcccg ttgaatatgg   840
ctcatggtg                                                           849
```

<210> SEQ ID NO 26
<211> LENGTH: 849
<212> TYPE: DNA
<213> ORGANISM: Artificial Sequence
<220> FEATURE:
<223> OTHER INFORMATION: Synthetic

<400> SEQUENCE: 26

```
gtccgacctg tcagctgcta gtcgtgcgga tcctgtcaga aaaactcatc gagcatcaaa      60
tgaaactgca atttgttcat atccggatta tcaataccat attttttgaaa aagccgtttc    120
tgtaatgaag acaaaactc accgaggcag ttccatagga tggcaagatc ctggtatcgg      180
tctgcgattc cgactcgtcc aacatcaata caacctatta atttcccctc gtcaaaaata    240
aggttatcaa gtgagaaatc accatgagtg acgactgaat cccgtgagaa tggcaaaagt    300
ttatgcattt cttccagac ttgttcaaca ggccagccat tacgctcgtc atcaaaatca    360
ctcgcatcaa ccaacccgtt attcattcgt gattgcgcct gagcgagacg aaatacgcga    420
tcgctgttaa aaggacaatt acaaacagga atcgaatgca accggcgcag gaacactgcc    480
agcgcatcaa caatattttc acctgaatca ggatattctt ctaatacctg gaatgctgtt    540
tttccgggga tcgcagtggt gagtaaccat gcatcatcag gagtacggat aaaatgcttg    600
atggtcggaa gaggcataaa ttccgtcagc cagtttagtc tgaccatctc atctgtaaca    660
tcattggcaa cgctaccttt gccatgtttc agaaacaact cgggcgcatc gggcttccca    720
tacaagcgat agattgtcgc acctgattgc ccgacattat cgcaagccca tttataccca    780
tataaatcag catccatgtt ggaatttaat cgcggcctcg acgtttcccg ttgaatatgg    840
ctcatggtg                                                             849
```

<210> SEQ ID NO 27
<211> LENGTH: 843
<212> TYPE: DNA
<213> ORGANISM: Artificial Sequence
<220> FEATURE:
<223> OTHER INFORMATION: Synthetic

<400> SEQUENCE: 27

```
gtcctgccag ctgctattcg gggggatcct gttagatcct tcatcgagca tcatatgaaa      60
ctgcaattta ttcatatcag gattatcaat accatatttt tgaaaaagct ttttctgcaa    120
tgaccgaaaa aactcaccga ggcagttcca taggatggca agatcctggt atcggtctgc    180
gattccgact cgtccaacat caatacaacc tattatttcc cctcgtcaaa ataaggtta     240
tcaagagaga atctccatg agtgacgact gaattttgta agaatggcaa aagtttatgc    300
atttcttttcc agacttgatc aacaggccag ccattacgct cgtcatcaaa tcactcgca    360
tcaaccaacc cgttattcat tcgtgattgc gcctgagcga gacgaaatac gcgatcgctg    420
ttaaaaggac aattacaaac aggaatcgaa tgcaaccggc gcaggaacac tgccagcgca    480
tcaacaatat tttcacctga atcaggatat tcttctaata cctggaatgc tgtttttccg    540
gggatcgcag tggtgagtaa ccatgcatca tcaggagtac ggataaaatg cttgatggtc    600
ggaagaggca taaattccgt cagccagttt agtctgacca tctcatctgt aacatcattg    660
gccacgctac ctttgccatg tttcagaaac aactctggcg catcgggctt cccatacaag    720
cgatagattg tcgcacctga ttgcccgaca ttatcgcgag cccatttata cccatataaa    780
tcagcatcca tgttggaatt taatcgcggc ctcgacgttt cccgttgaat atggctcatg    840
gtg                                                                   843
```

<210> SEQ ID NO 28
<211> LENGTH: 872
<212> TYPE: DNA
<213> ORGANISM: Artificial Sequence
<220> FEATURE:
<223> OTHER INFORMATION: Synthetic

```
<400> SEQUENCE: 28
gtccgtcctg tcagctgcta gtcgtgcgga tcctgttaga aaaactcatc gagcatcaaa      60
tgaaactgca atttattcat atcaggatta tcaataccat attttttgaaa aagccgtttc    120
tgtaatgaag gagaaaactc accgaggcag ttccatagga tggcaagatc ctggtatcgg    180
tctgcgattc cgactcgtcc aacatcaata caacctatta atttcccctc gtcaaaaata    240
aggttatcaa gtgagaaatc accatgagtg acgactgaat ccggtgagaa tggcaaaagt    300
ttatgcattt ctttccagac ttgttcaaca ggccagccat tacgctcgtc atcaaaatca    360
ctcgcatcaa ccaaaccgtt attcattcgt gattgcgcct gagcgagacg aaatacgcga    420
tcgctgttaa aaggacaatt acaaacagga atcgaatgca accggcgcag gaacactgcc    480
agcgcatcaa caatattttc acctgaatca ggatattctt ctaatacctg gaatgctgtt    540
tttccgggga tcgcagtggt gagtaaccat gcatcatcag gagtacggat aaaatgcttg    600
atggtcggaa gaggcataaa gtcccgtcag ccagtttagt ctgaccatct catctgtaac    660
atcattggca acgcttacct ttgccatgtt ttcagaaaca actctggcgc atcgggcttc    720
ccaatacaag cgatatgatt gtccgcaccc gagtgccccg acatttatcg cggaggccca    780
ttttataccc attataaaat caccatccca tgtttgggaa tttaatcggc gggcctccaa    840
cgtttccccg gttgaatatg gcttctaggg tg                                  872

<210> SEQ ID NO 29
<211> LENGTH: 862
<212> TYPE: DNA
<213> ORGANISM: Artificial Sequence
<220> FEATURE:
<223> OTHER INFORMATION: Synthetic

<400> SEQUENCE: 29
gtccgtcctg tcagctgcta gtcgtgcgga tcctgttaga aaaactcatc gagcatcaaa      60
tgaaactgca atttattcat atcaggatta tcaataccat attttttgaaa aagccgcttc    120
tgtaatgaag gagaaaactc accgaggcag ttccatagga tggcaagatc ctggtatcgg    180
tctgcgattc cgactcgtcc aacatcaata caacctatta atttcccctc gtcaaaaata    240
aggttatcaa gtgagaaatc accatgagtg acgactgaat ccggtgagaa tggcaaaagt    300
ttatgcattt ctttccagac ttgttcaaca ggccagccat tacgctcgtc atcaaaatca    360
ctcgcatcca ccaaaccgtt attcattcgt gattgcgcct gagcgagacg aaatacgcga    420
tcgctgttaa aaggacaatt acaaacagga atcgaatgca accggcgcag gaacactgcc    480
agcgcatcaa caatattttc acctgaatca ggatattctt ctaatacctg gaatgctgtt    540
tttccgggga tcgcagtggt gagtaaccat gcatcatcag gagtacggat aaaatgcttg    600
atggtcggaa gaggcataaa ttccgtcagc cagtttagtc tgaccatctc atctgtaaca    660
tcattggcaa cgctaccttt gccatgtttc agaaacaact cttggcgcat cggggcttcc    720
ccatacaagc gattagattt gtcgcaccct gattgccccg acctttatcg cgagcccatt    780
ttataccccat ataaatcagc atccatgttg gaaatttaat tcgcggcctc cgacgttttc    840
ccgttgaata tggctcatgg ga                                             862
```

INEXPENSIVE AUTONOMOUS ASSEMBLY OF ULTRA-LARGE (UL) DNA CONSTRUCTS

CROSS REFERENCE TO RELATED APPLICATIONS

This application is a nonprovisional application that derives from, and claims priority to, U.S. nonprovisional application Ser. No. 13/936,309 filed Jul. 9, 2013 which derived from and claimed priority to provisional patent application 61/669,295, which was filed Jul. 9, 2012, for "Inexpensive Autonomous Assembly of Ultra-Large (UL) DNA Constructs".

STATEMENT REGARDING FEDERALLY SPONSORED RESEARCH OR DEVELOPMENT

This invention was made with government support under a contract awarded by the United States Defense Advanced Research Project Agency (HR0011-12-C-0064). The government has certain rights in the invention.

THE NAMES OF THE PARTIES TO A JOINT RESEARCH AGREEMENT

Not applicable

INCORPORATION-BY-REFERENCE OF MATERIAL SUBMITTED ON A COMPACT DISC

None

BACKGROUND OF THE INVENTION (1) Field of the Invention

This invention is in the field of nucleic acid chemistry, more specifically the synthesis of nucleic acids, more specifically to the synthesis of large DNA molecules, and more specifically to processes and procedures that create large (more than 1000 base pairs) double-stranded DNA via the assembly of large numbers of short single stranded DNA molecules having preselected sequences.

(2) Description of Related Art

Synthetic biology needs processes to enable low-cost and rapid assembly of many synthetic DNA fragments into large DNA assemblies. For example, in 2012, DARPA issued a small business grant solicitation seeking technology to assemble single-stranded synthetic fragments to give 20,000 bp ML-DNA constructs. A short while earlier, the Army Research Office issued a small business grant solicitation seeking companies to design software to allow 30,000 base pairs of single stranded DNA self-assemble to form nanostructures.

Unfortunately, the realities behind the biophysics of DNA make these goals fanciful, if the attempt is made with standard DNA. With just four nucleotides, the information density of standard DNA is too low to allow (without exquisite design) more than ca. a dozen single strands to self-assemble upon simple mixing. With more fragments containing only natural nucleotides, the vagaries of "strong" and "weak" G:C and A:T pairs, hairpins, off-target Watson-Crick hybridization, and non-Watson Crick interactions (e.g wobble and major groove binding) defeat self-assembly. These can be illustrated by mentioning the following problems:

Problem (A).

Different DNA base pairs do not contribute uniformly to duplex stability. The largest source of this non-uniformity in strand hybridization is a feature of standard DNA that joins A:T pairs by just two hydrogen bonds and G:C pairs by three. Thus, A:T pairs contribute to duplex stability consistently less than G:C pairs. This makes it challenging to design DNA fragments with different nucleotide compositions that hybridize to their complements with the same affinity.

Problem (B).

DNA strands can interact in ways outside of those specified by the canonical Watson-Crick pair. In addition to wobble pairing (e.g. G:T pairs), DNA can form major groove interactions (e.g. G-quartets). These, illustrated in FIG. 1 and FIG. 2, can (in appropriate contexts) be stronger than Watson-Crick pairing and can defeat pairing between large numbers of single stranded DNA molecules designed solely by applying Watson-Crick rules.

Problem (C).

Figure 3:
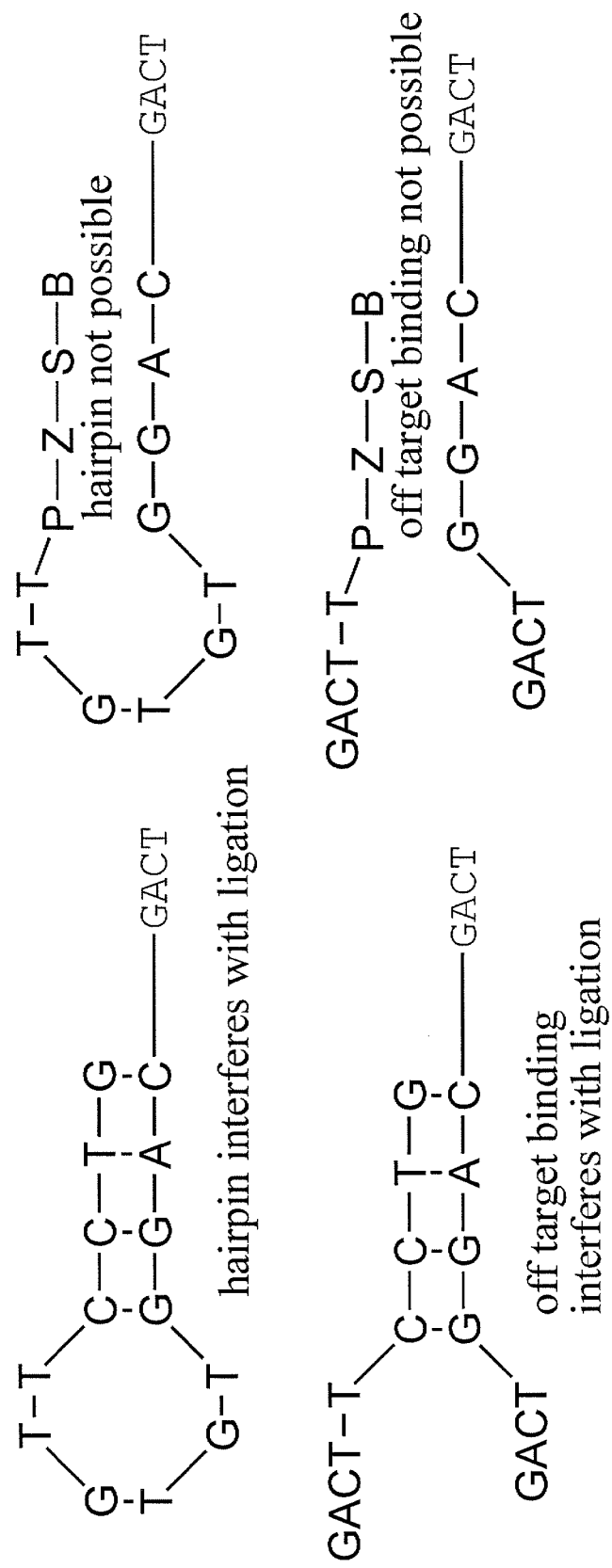

Intra-strand folding can defeat desired inter-strand interactions needed for hybridization, primer extension, and ligation. Hairpin structures formed by a single strand, for example, can easily disrupt inter-strand hybridization that intended for a multi-strand assembly (FIG. 3). The easy accessibility of hairpins can be illustrated by some simple mathematics. The 5'-nucleotide of a standard DNA molecule must be G, A, T, or C. Whatever it is, it can find a complementary C, T, A, or G (respectively) with a one-in-four probability at each base farther into the sequence. Within a random sequence 64 nucleotides in length, the final one, two, and three nucleotides will find perfect complements 16 times, 4 times, and once within that sequence, on average. These will form hairpins with stems that are joined by one, two, and three perfect base pairs respectively. Stems with four or five pairs and loops of 2-5 nucleotides are adequate to disrupt hybridization. Therefore, loops must be avoided by design, and this design becomes difficult to manage as the number of fragments increase.

Problem (D):

Even if DNA had access only to Watson-Crickery, even if all nucleobase pairs contributed equally to duplex stability, and even if single strands never folded by themselves, the autonomous self-assembly problem would still not be trivial. With only four nucleotide letters to encode information, the information density of natural DNA is low. For a bacterial sized genome having a random sequence, all 10mers are present once. Overlapping 10mers are more than adequate to support ligation, even if they include one or two mismatches, at temperatures when typical ligases operate. This low information density makes it essentially impossible to do reliable self-assembly from any more than a dozen or so fragments. Each complement is present at low concentrations, making the rates at which they find each other low a priori. The rate of hybridization is slowed as GACT DNA fragments find "off target" GACT fragments, bind to them, and dwell for a time before dissociating to seek their "on target" fragments.

Given these realities of the chemical structure of natural DNA, it is hardly surprising that Nature rarely does what synthetic biologists want to do: Large-scale assembly by way of the hybridization of multiple single stranded fragments. Non-uniformity in the binding of sequences of natural nucleotides make it essentially impossible to assemble by autonomous hybridization of thousands (or more) nucleobase pairs, even if the primary products have no errors at all. Therefore, in natural biology, large-scale DNA assemblies are carried forward carefully from generation to generation, with strand displacement at the core of polymerization and specifically targeted ligation events that do not allow the DNA to wander into multiple single strands.

Thus, most large synthetic DNA (LS-DNA) molecules today are obtained via the "Gibson method" [Gibson 2011], rather than the spontaneous self-assembly of many single DNA strands prepared by synthesis. The Gibson method reproduces in vitro the natural Szostak process for recombination in vivo [Szostak et al. 1983]. It starts with pre-annealed duplexes, cuts them back with a 3'-exonuclease to generate sticky ends (without cutting back so far as to disrupt the duplex) and then uses the resulting sticky ends to assemble the duplexes with overhangs. Expert intervention is required at many steps in the process, creating costs.

While [Gibson 2011] speaks of single strand assembly, including single stranded assembly in yeast cells [Gibson 2009], they teach that to "ensure that error-free molecules are obtained at a reasonable efficiency, only eight to twelve 60-base oligos are assembled at one time" [Gibson 2011]. This teaching, we presume, reflects the problems listed above, which are deeply embedded in the molecular structure of natural DNA. These drive the need for inventive processes to allow LS-DNA assembly from multiple single stranded synthetic DNA fragments.

BRIEF SUMMARY OF THE INVENTION

This invention provides processes to assemble more than 12, and preferably at least 20, strands of single stranded DNA fragments, preferably 50-100 nucleotides in length, and more preferably 50-80 nucleotides in length, to give large synthetic DNA (LS-DNA) constructs. Those fragments intended to be ligated must have free 5'-phosphate groups at the ends to be ligated and/or free 3'-hydroxyl groups at the ends to be ligated. Those fragments intended to be extended must have free 3'-hydroxyl groups at the ends to be extended. Further, only those 3'-ends annealed to another of the DNA fragments with a 3'-underhang will be extended (FIGS. 5-10). As useful applications, this invention therefore allows the assembly, from a collection of single stranded DNA fragments, of genes encoding whole proteins (typically 1000-3000 nucleotide pairs), plasmid-sized constructs (5000-10000 base pairs), artificial chromosomes (such as BACs having 10,000 to 300,000 nucleotide pairs), or even chromosomes (having a million or more nucleotide pairs).

BRIEF DESCRIPTION OF THE SEVERAL VIEWS OF THE DRAWING(S)

FIG. 1. Illustration of Problem (A). Wobble pairing can cause single stranded oligonucleotides to not interact as predicted by Watson-Crick rules, especially in an annealing attempt that involves more than 12 single stranded oligonucleotides (and certainly 20 or more). As AEGIS pairs are all joined by three hydrogen bonds, AEGIS pairs are stronger than A:T pairs, allowing correct pairs to dominate over wobble, which involve two hydrogen bonds [Benner et al. 2010].

Figure 2:
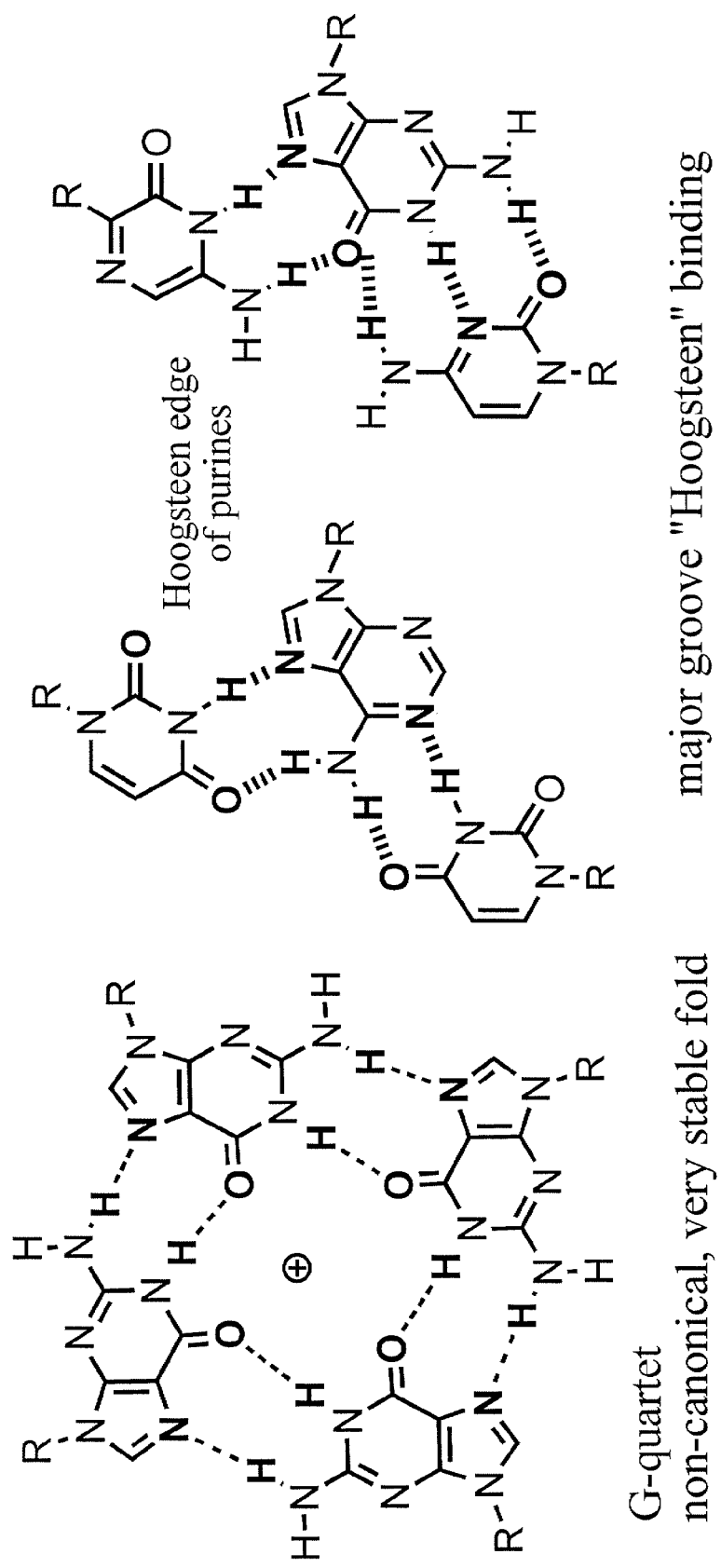

FIG. 2. Further illustration of Problem (A). Major groove binding interactions can cause single stranded oligonucleotides to not anneal as predicted by Watson-Crick pairing, especially if the annealing attempt involves more than 12 single stranded oligonucleotides (and certainly 20 or more). Various of the AEGIS purines cannot form these major groove interactions, if they are implemented in a form that lacks a nitrogen atom at what would be formally called "position 7" on the analogous purine. These include P and 7-deazaisoguanosine.

FIG. 3. Illustration of Problem (B). Hairpins prevent certain single stranded oligonucleotides from interacting with their target as predicted by Watson-Crick pairing. Hairpins that involving a folding back of the 3'-end also can be extended by polymerases to give undesired products. While hairpins can be avoided by careful design if only a few oligonucleotides are being assembled, they are difficult to avoid by design if the assembly attempt involves more than 12 single stranded oligonucleotides (and certainly for 20 or more). Hairpins cannot form if the ends contain AEGIS components (shown in cartoon form).

Figure 4:
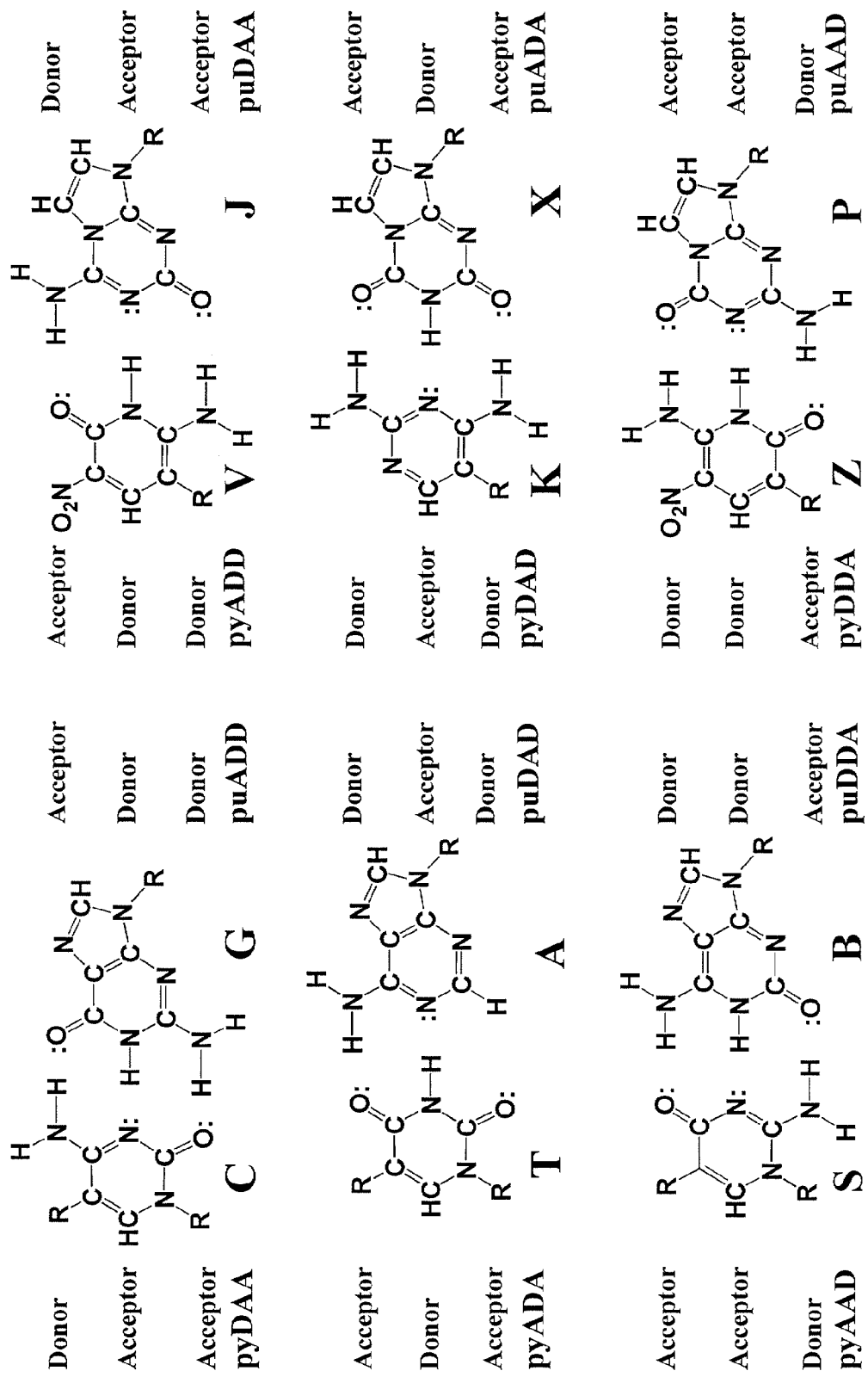

FIG. 4. Watson-Crick pairing follow two complementarity rules: (a) size (large purines pair with small pyrimidines) and (b) hydrogen bonding (on purine pu and pyrimidine py ring analogs, hydrogen bond acceptors, A, pair with donors D). Rearranging D and A groups on the nucleobases creates artificially expanded genetic information systems (AEGIS). A central teaching of this application is that various heterocyclic systems can implement the same hydrogen bonding interaction. For example, isoguanine and 7-deazaisoguanine both implement the puDDA hydrogen bonding pattern.

Figure 5A:
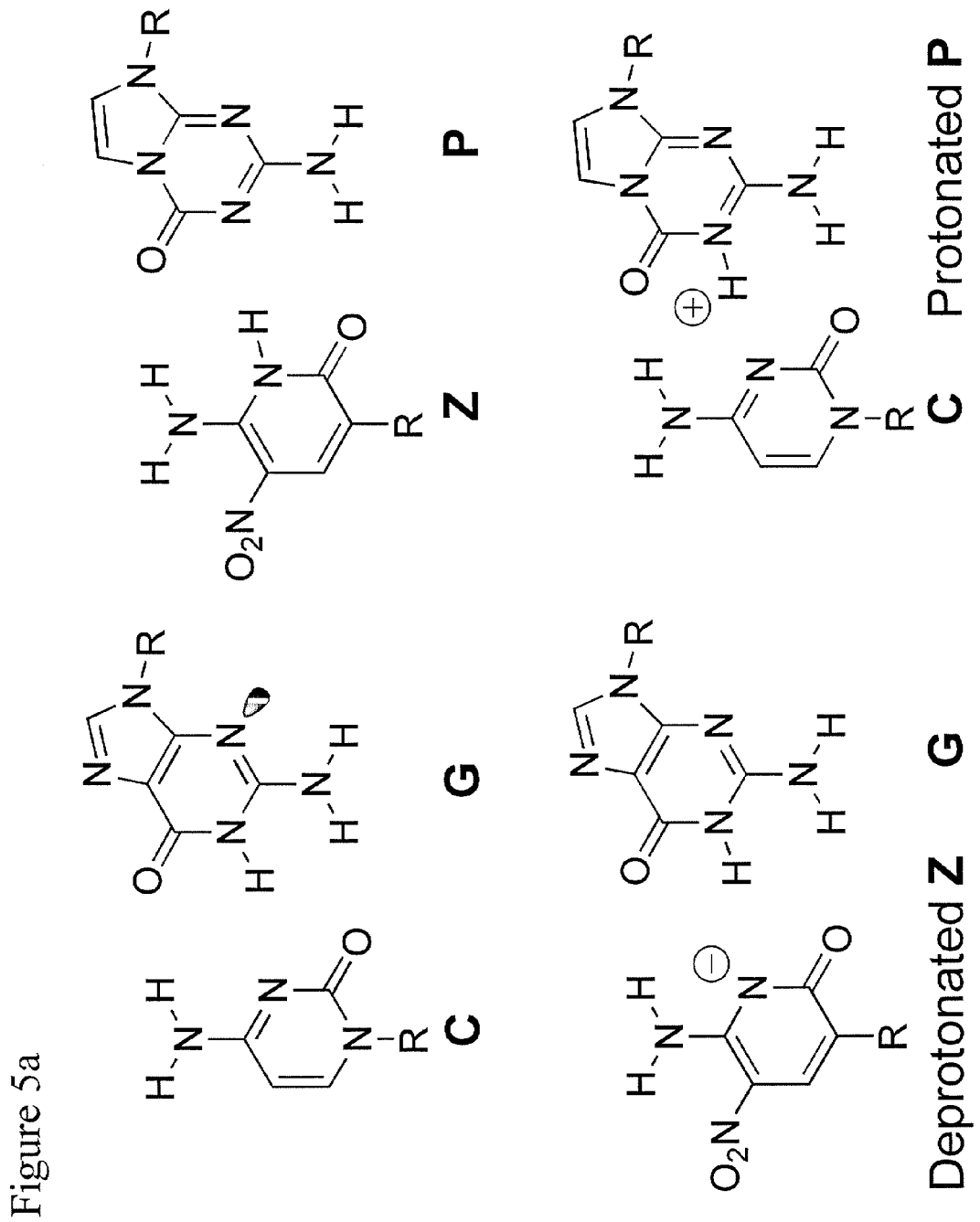
Figure 5B:
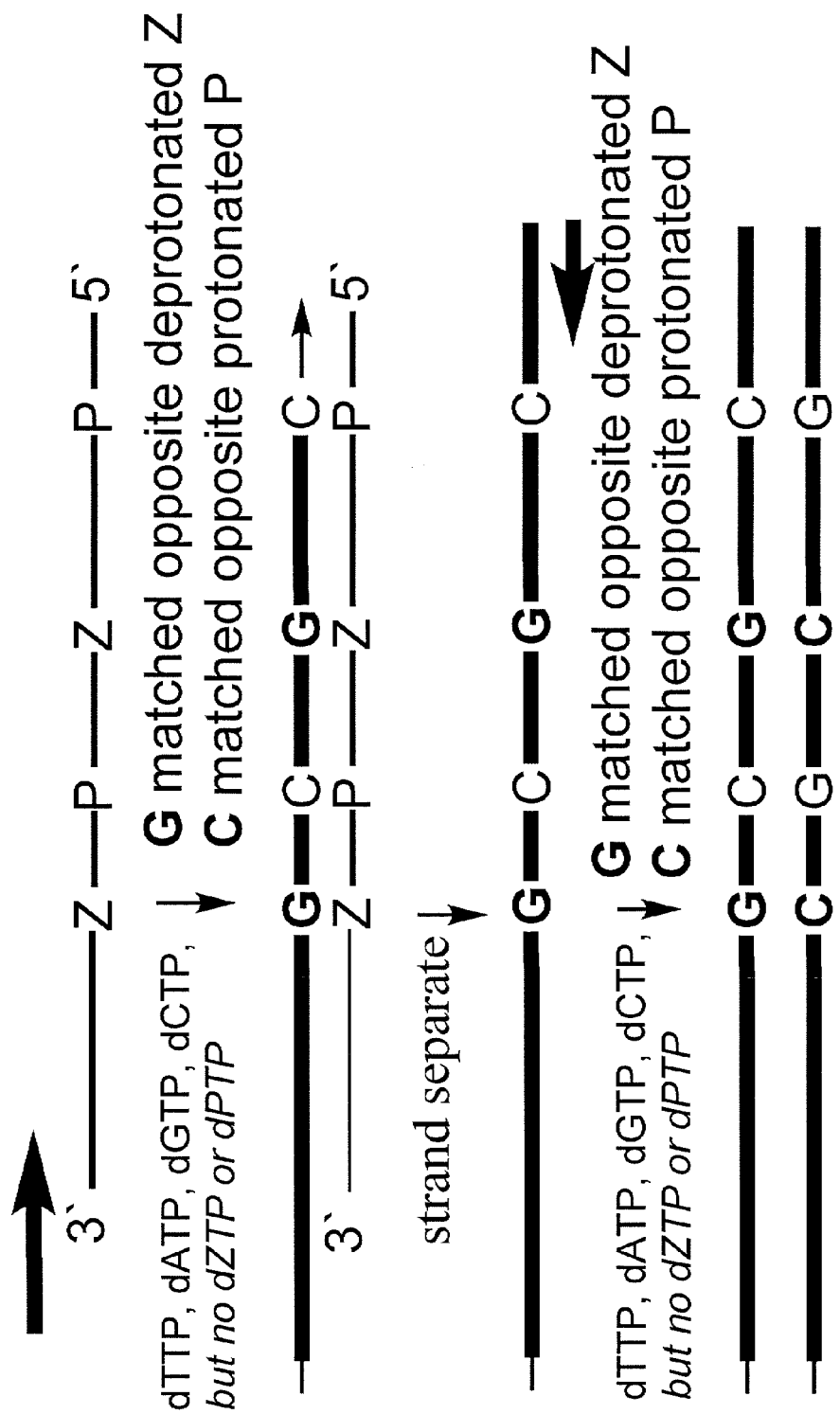

FIG. 5. (a) Proposed chemical mechanisms for the overall conversion of Z:P pairs to C:G pairs, completed with two copying steps. (b) Copying steps are shown, where the first polymerase extension cycle creates a natural strand by placing C opposite P and G opposite B. Alternatively, if dZTP or dPTP is present in small amounts, the conversion can be completed in three or more cycles, or in the products of PCR amplification.

Figure 6A:
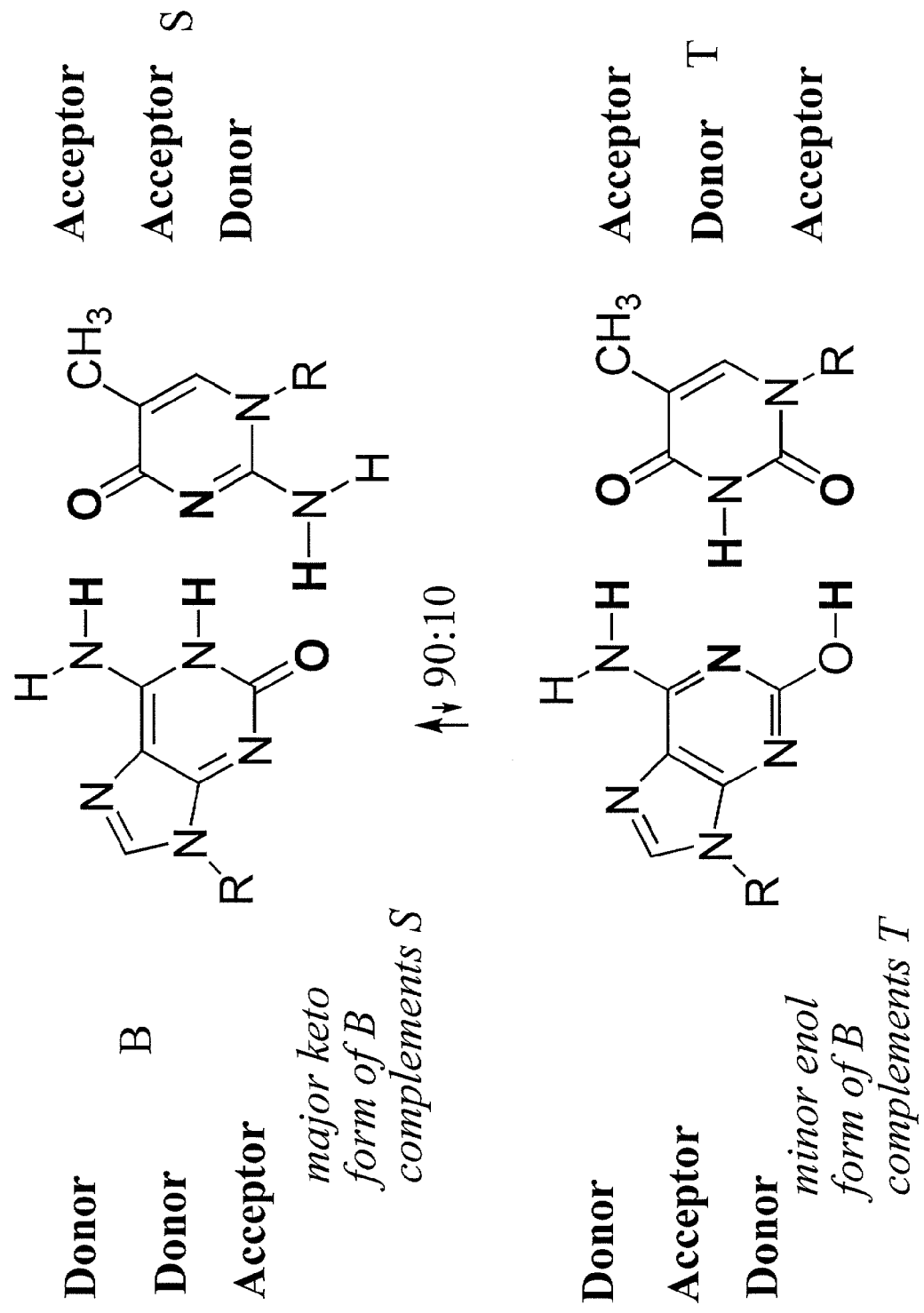
Figure 6B:
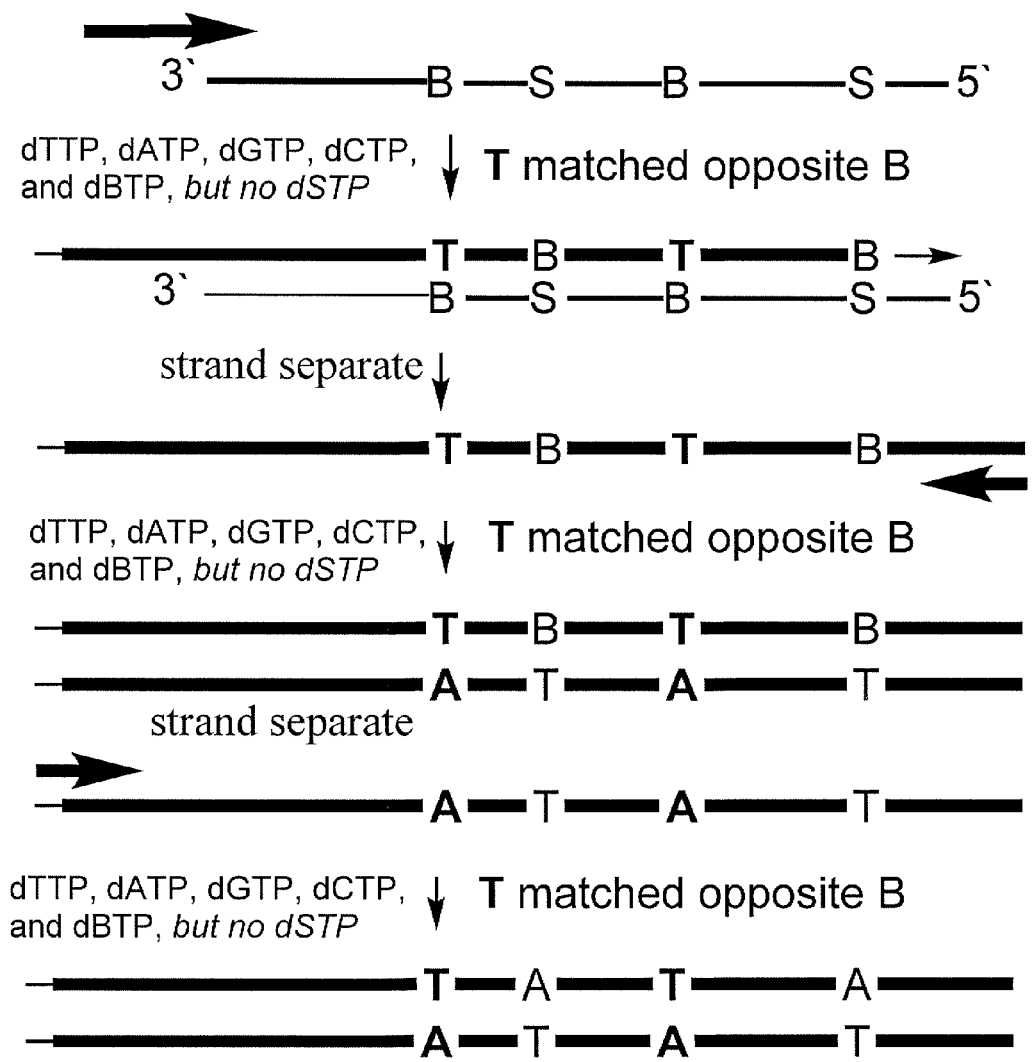

FIG. 6. (a) Proposed chemical mechanisms for the overall conversion of S:B pairs to T:A pairs, completed with three copying steps, where the minor enol tautomer of isoG pairs with T. (b) Copying steps shown involve three cycles, where a small amount of dBTP is incorporated to allow the dS in the ligated product to first be copied with a dB.

Figure 7:
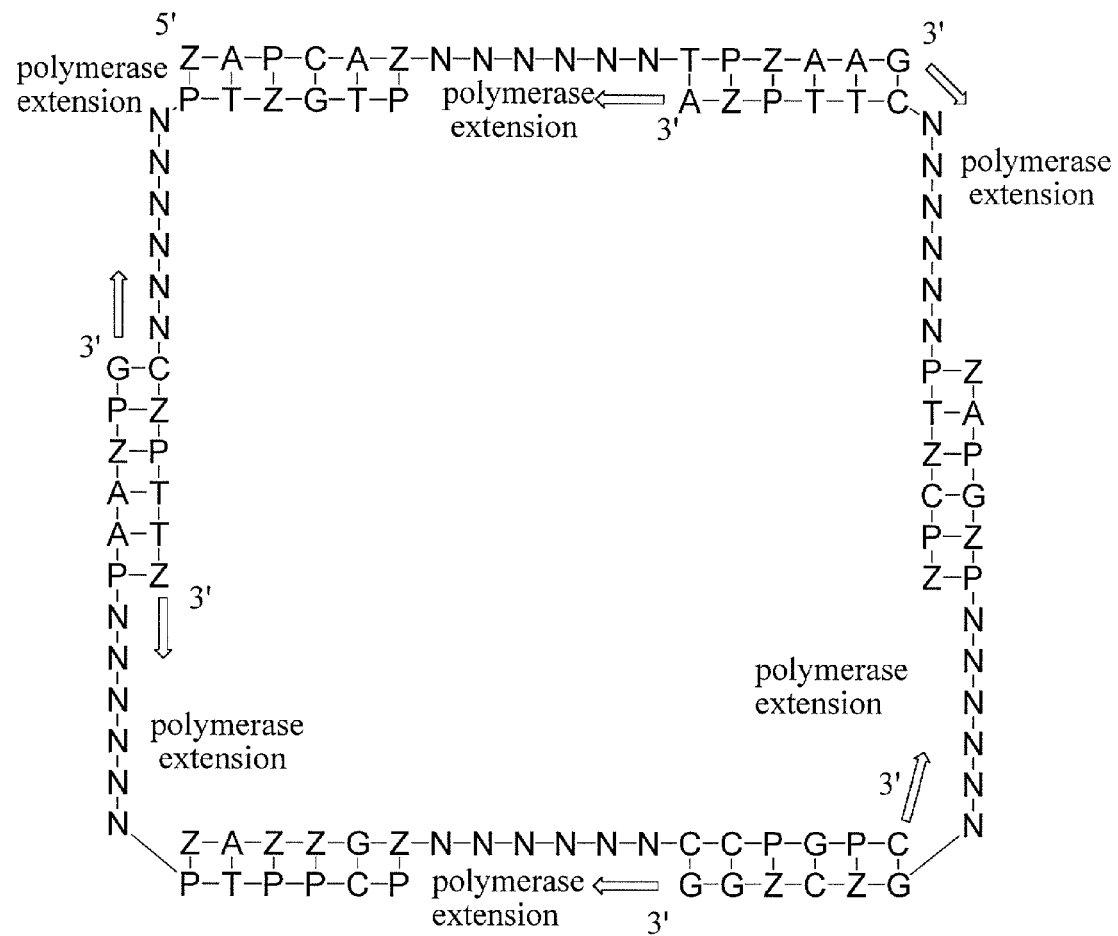

FIG. 7. Cartoon illustrating the annealing and extension parts of the anneal-extend-ligate process using AEGIS components and a hypothetical cyclic target. The AEGIS components shown are Z and P; analogous cartoons can be drawn using the AEGIS components S and B. The DNA strands are preselected to have regions that "partially overlap", meaning that the 3'-end of one or more of the fragments anneals to another fragment so that its 3'-end can be extended using its annealed partner as a template. The overlapping annealed segments preferably have two or more AEGIS components, although a single AEGIS component is not excluded. The extension must be done by a polymerase that is not "strand displacing"; an example is Phusion DNA polymerase. Shown are not actual sequences, but rather generic sequences to illustrate the concept; therefore sequence listing entries are not required by statute, regulations, or USPTO procedures. In practice, the paired regions are longer (presently preferred 12-20 nucleotides, more preferably 15-18, with similar melting temperatures), and the single stranded regions to be copied are longer. The presently preferred total length of the fragments is 40-100 nucleotides, more preferably 50-80 nucleotides, and most preferably 50-60 nucleotides, with the preferred length dependent on the level of error in the synthetic DNA fragments themselves.

Figure 8:
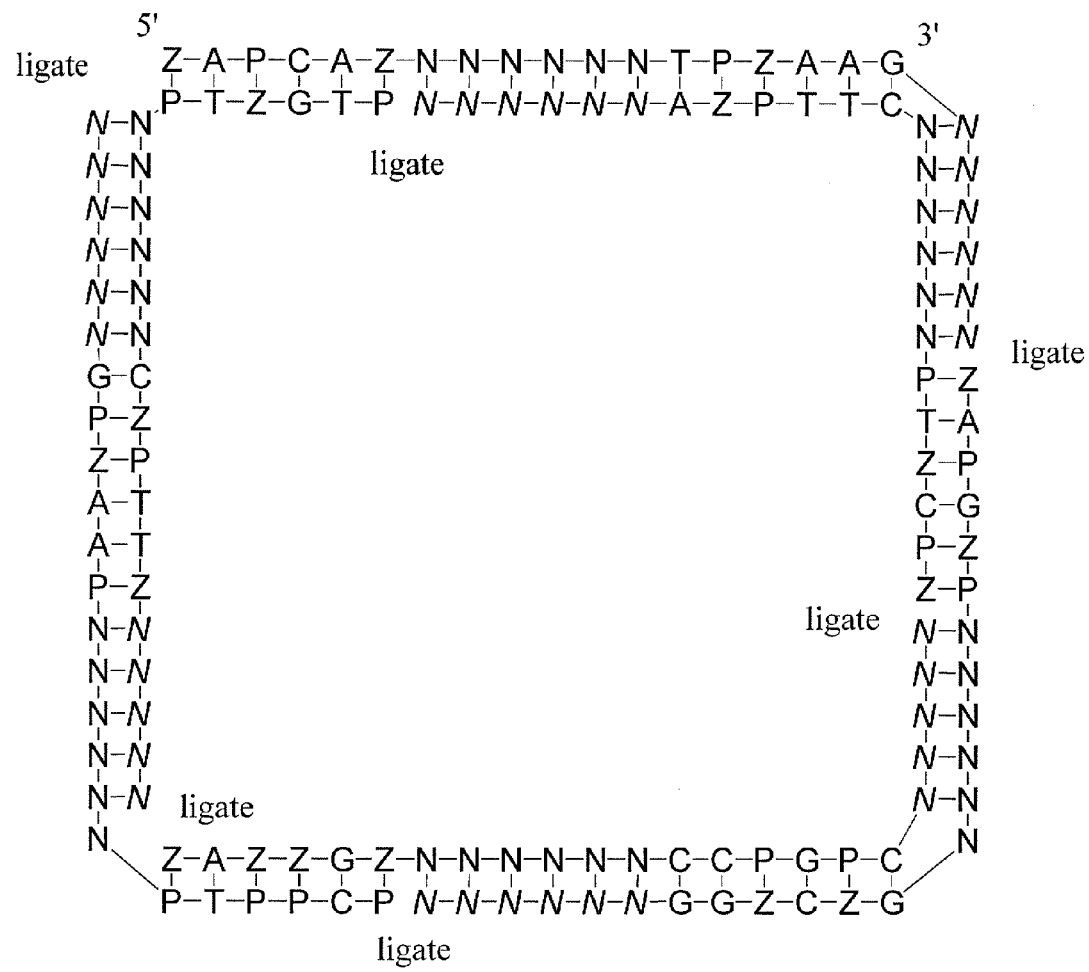

FIG. 8. Cartoon illustrating the extended products ready for the ligation part of the anneal-extend-ligate process using AEGIS components and a hypothetical cyclic target. N's in italics are those added by the polymerase against the N's in the preselected sequence. These are not actual sequences, but rather generic sequences to illustrate the concept; therefore sequence listing entries are not required by statute, regulations, or USPTO procedures. In practice, the paired regions are longer (presently preferred 12-20 nucleotides, more preferably 15-18, with similar melting temperatures), and the single stranded regions to be copied are longer. The presently preferred total length of the fragments is 40-100 nucleotides, more preferably 50-80 nucleotides, and most preferably 50-60 nucleotides, with the preferred length dependent on the level of error in the synthetic DNA fragments themselves.

Figure 9:
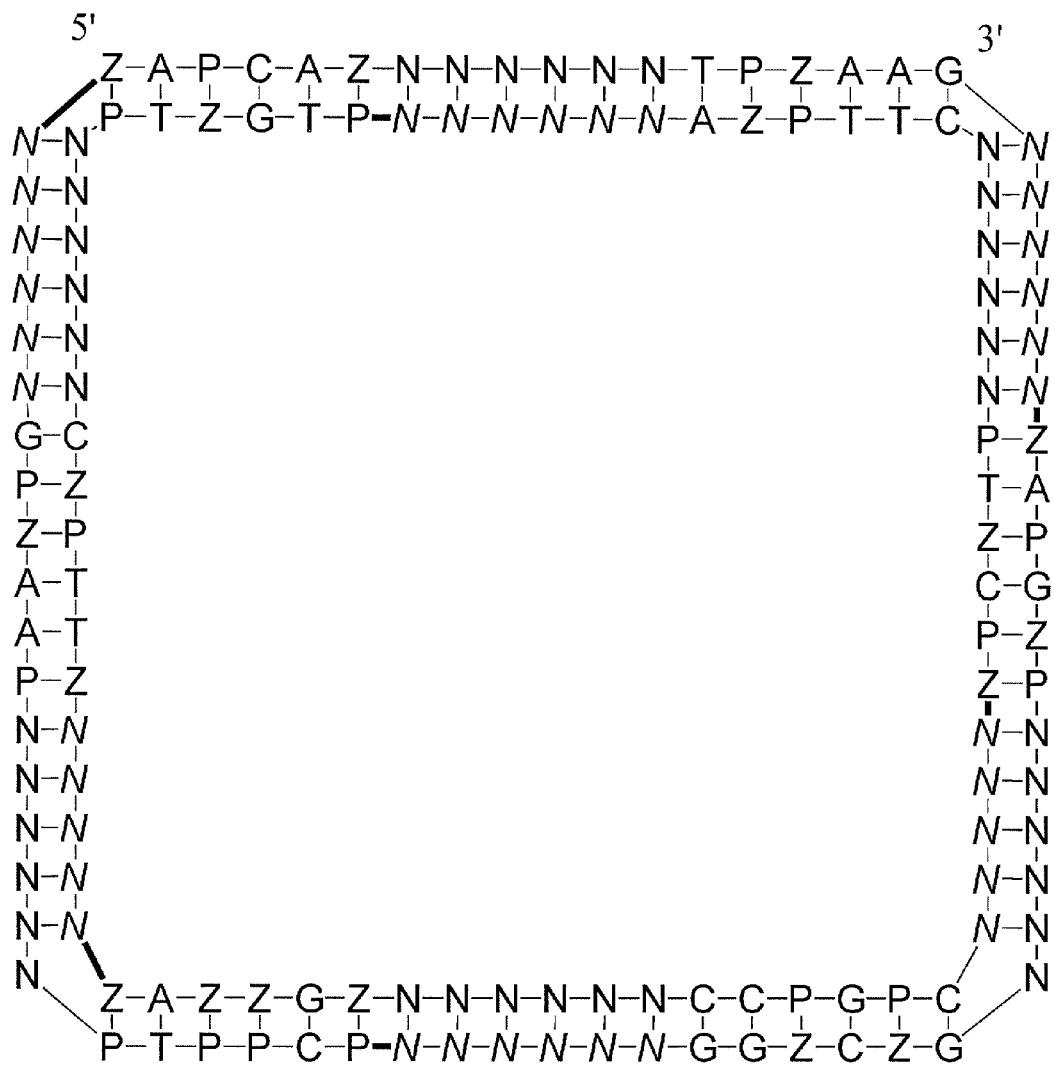

FIG. 9. Cartoon illustrating the product after ligation of the anneal-extend-ligate process using AEGIS components and a hypothetical cyclic target. These are not actual sequences, but rather generic sequences to illustrate the concept; therefore sequence listing entries are not required by statute, regulations, or USPTO procedures. In practice, the paired regions are longer (presently preferred 12-20 nucleotides, more preferably 15-18, with similar melting temperatures), and the single stranded regions to be copied are longer. The presently preferred total length of the fragments is 40-100 nucleotides, more preferably 50-80 nucleotides, and most preferably 50-60 nucleotides, with the preferred length dependent on the level of error in the synthetic DNA fragments themselves.

Figure 10:
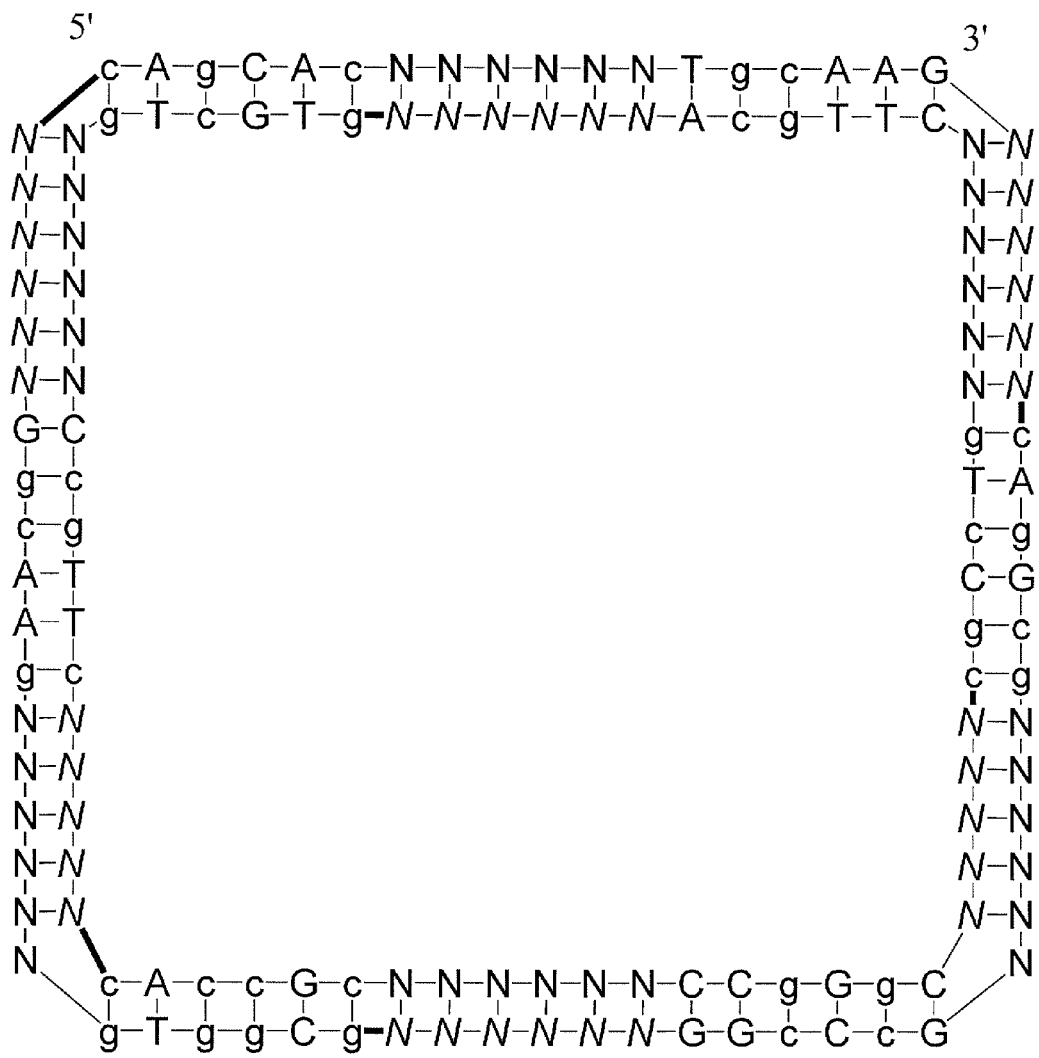

FIG. 10. Cartoon illustrating the conversion step following the anneal-extend-ligate process using AEGIS components and a hypothetical cyclic target. Lower case nucleotides are those that arose from conversion. These are not actual sequences, but rather generic sequences to illustrate the concept; therefore sequence listing entries are not required by statute, regulations, or USPTO procedures. This is illustrated with Z:P conversion; see Example 1 for S:B conversion. In practice, the paired regions are longer (presently preferred 12-20 nucleotides, more preferably 15-18, with similar melting temperatures), and the single stranded regions to be copied are longer. The presently preferred total length of the fragments are 40-100 nucleotides, more preferably 50-80 nucleotides, and most preferably 50-60 nucleotides, with the preferred length dependent on the level of error in the synthetic DNA fragments themselves.

DETAILED DESCRIPTION OF THE INVENTION

(1) Use of Non-Standard Nucleotides to Address the Problems in Multi-Fragment Assembly The instant invention add nucleotides to the "alphabet" of standard DNA, specifically, components of an artificially expanded genetic information systems (AEGIS) (FIG. 4). By shuffling hydrogen bond donor and acceptor groups, AEGIS adds up to eight nucleotides to the four (G, A, T and C) found in standard DNA. These form four orthogonal additional pairs between AEGIS complements that allow AEGIS DNA to bind to complementary DNA but not to standard GACT DNA [Benner et al. 2010] joined by "non-standard hydrogen bonding patterns" These are illustrated in FIG. 4, with the hydrogen bonding pattern defined by the prefix "py" (to indicate a heterocycle with a single six-membered ring) or "pu" (to indicate a heterocycle with a single six membered ring fused to a single five-membered ring) followed by "donor" or "acceptor", proceeding from the major groove to the minor groove. The pattern is "non standard" if it differs from the patterns of hydrogen bonding groups found in G, A, aminoA, C, T, or U, or other heterocycles that implement the same hydrogen bonding pattern, regardless of the choice of the heterocycle upon which to implement that hydrogen bonding pattern. A teaching of this specification is that the same hydrogen bonding pattern can be implemented by more than one heterocycle.

AEGIS pairs have been designed to not suffer from many of the problems found in natural DNA. First, all nucleobase pairs are joined by three hydrogen bonds (FIG. 4), addressing Problem (A) in natural DNA. This means that AEGIS nucleobase pairs are not sometimes strong and sometimes weak (the standard C:G pair is strong; the T:A pair is weak), but rather are uniformly strong.

Second, the AEGIS nucleobases are designed so as to not have Hoogsteen and other major groove non-canonical hydrogen bonding possibilities (FIG. 2). Thus, in regions where AEGIS nucleotides are incorporated, Problem (B) cannot confound desired hybridization.

Third, adding nucleotide letters to an expanded genetic alphabet increases the information density of the resulting DNA sequences, addressing Problem (D). With six or eight different nucleotide letters, and certainly with 10 or 12, even a mixture of 10,000 fragments, each 100 nucleotides long, does not have close "off-target" mismatches that can, kinetically, slow the rate of hybridization or, thermodynamically, generate undesired hybrids that compete with the formation of desired hybrids.

The added information density can be used strategically to solve Problem (C). For example, if a segment of DNA is built entirely from standard GACT nucleotides, and if AEGIS nucleotides are at the ends where ligation will take place, it is impossible for hairpin structures to form, and therefore impossible for hairpin structures to compete with desired ligation (FIG. 3).

As reduction to practice, the oligonucleotides built from AEGIS components are prepared by standard phosphoramidite-based phosphoramidite synthesis from phosphoramidites [Yang et al 2011, and references cited therein]. These procedures are described in the following publications and patents, and publications that these cite, all incorporated in their entirety by reference.

(2) Optional Conversion

Of course, any construct that has self-assembled autonomously around AEGIS fragments will not at this point be completely natural DNA. It will contain unnatural AEGIS nucleotides embedded throughout the LS-DNA construct.

This unnaturalness need not necessarily limit the application of such constructs should bacteria become available that accept AEGIS DNA. Nor will it be an issue should the constructs be used to support nanostructures that need not enter natural biological systems downstream.

However, many synthetic biologists want entirely natural LS-DNA constructs. Therefore, the process of the invention can optionally include a step that converts AEGIS pairs to give standard pairs. This conversion exploits the recipes disclosed in U.S. patent application Ser. No. 12/653,613, which is incorporated in its entirety herein by reference. While not wishing to be bound by theory, the key to this conversion is the ability of a polymerase, if it does not have available a complementary non-standard nucleoside triphosphate, to create the best Watson-Crick mismatch between a non-standard AEGIS component in a template and a standard nucleotide, based on (for example) alternative protonation/deprotonation states and/or alternative tautomeric forms.

Conversion in its various embodiments is exemplified by two examples, one involving the dZ:dP pair, and the other involving the dS:dB AEGIS pair. While not wishing to be bound by theory, protonation of the dC:dP mismatch allows the misincorporation of dC by a polymerase opposite dP in a template (FIG. 5) in the absence of a complement to the template dP. Deprotonation of the dG:dZ mismatch allows the misincorporation of dG by a polymerase opposite dZ in a template, again in absence of dPTP. In the next cycle of copying, the newly incorporated C then directs the incorporation of dG, finishing the conversion of dP:dZ pairs to dG:dC pairs.

Polymerases can, again according to theory, use this deprotonated pair to direct the misincorporation of dG opposite dZ in a template In the next cycle of copying, the newly incorporated dG then directs the incorporation of dC, finishing the conversion of dZ:dP pairs to dC:dG pairs. This can be done in two or three steps, three steps if small amounts of dZTP and/or dPTP are added.

While not wishing to be bound by theory, for dS and dB, a minor tautomeric form of the puDDA hydrogen bonding pattern, when implemented using the isoguanine heterocycle, supports a mismatch with thymine (FIG. 6). Polymerases can, again according to theory, use this minor tautomer to direct the misincorporation of dT opposite dB in a template in the absence of a complement to the major tautomer of isoguanine. In the next cycle of copying, the newly incorporated dT then directs the incorporation of dA, finishing the conversion of dS:dB pairs to dT:dA pairs.

Since dS does not have an analogous mechanism to support an dS:dA mismatch, the presently preferred conversion process includes a small amount of disoGTP, to match to disoC in the template. The newly incorporated isoguanine then, in its minor tautomeric form, is mismatched against thymine, and the overall conversion of these dS:dB pairs to dT:dA pairs is completed with three copying steps.

Conversion can also be effected with RNA assemblies involving reverse transcriptase, and other implementations of the AEGIS non-standard hydrogen bonding schemes.

Thus, after autonomous self-assembly of independently synthesized fragments using the orthogonality of AEGIS nucleotides, the AEGIS nucleotides are removed to give an entirely natural full-length DNA product. Of course, the synthetic fragments must be designed so as to have Z present at sites where C is desired in the final LS-DNA product, P is present at sites where G is desired in the final LS-DNA product, S is present at sites where T is desired in the final LS-DNA product, and B is present at sites where A is desired in the final LS-DNA product. Additional rules can be specified depending on the nature of the conversion process.

(3) References

Benner, S. A., Yang, Z., Chen, F. (2010) Synthetic biology, tinkering biology, and artificial biology. What are we learning? Comptes Rendus 14, 372-387
Benner, S. A. (2010) Non-standard nucleobases implementing the isocytidine and isoguanosine hydrogen bonding patterns. U.S. Pat. No. 7,741,294
Gibson, D. G. (2009) Synthesis of DNA fragments in yeast by one-step assembly of overlapping oligonucleotides. *Nucl. Acids Res.* 37, 6984-6990.
Gibson, D. G. (2011) Enzymatic assembly of overlapping DNA fragments. *Methods Enzymol.* 498, 349-361
Szostak, J. W., Orrweaver, T. L., Rothstein, R. J., Stahl, F. W. (1983) The double-strand-break repair model for recombination. *Cell*: 33, 25-35
Yang, Z., Chen, F., Chamberlin, S. G., Benner, S. A. (2010) Expanded genetic alphabets in the polymerase chain reaction. Angew. Chem. 49, 177-180
Yang, Z., Chen, F., Alvarado, J. B., Benner, S. A. (2011) Amplification, mutation, and sequencing of a six-letter synthetic genetic system. *J. Am. Chem. Soc.* 133, 15105-15112

(4) Examples

Synthesis of Preselected DNA Oligonucleotide Fragments

The invention was demonstrated by the assembly of a gene that encodes a protein that confers resistance on kanamycin. The following fragments were synthesized on solid phase.

```
                                            SEQ ID NO 01
CACCATGAGCCATATTCAACGGGAAACGTCGAGGCCGCGATTAAATTCCAA

CATGGASGCSGASTT

SEQ ID NO 02
SGASTGCCCGACBTTATCGCGAGCCCATTTATACCCATATAABTCBGCBTC

C

SEQ ID NO 03
SGTCGGGCABTCBGGTGCGACAATCTATCGCTTGTATGGGAAGCCCGASGC

GCCBGAG

SEQ ID NO 04
BACBTCBTTGGCBACGCTACCTTTGCCATGTTTCAGAAACAACTCSGGCGC

BT

SEQ ID NO 05
SGCCAASGASGTSACAGATGAGATGGTCAGACTAAACTGGCTGACGGABTT

TATGCCSCTSC

SEQ ID NO 06
TCBTCBGGBGTBCGGATAAAATGCTTGATGGTCGGBAGBGGCATAAAST

SEQ ID NO 07
SACSCCSGASGATGCATGGTTACTCACCACTGCGATCCCCGGBAAAACBGC

BTT

SEQ ID NO 08
CBACAATBTTSTCBCCTGAATCAGGATATTCTTCTAATACCTGGAASGCSG

TTTTSC

SEQ ID NO 09
SGABAASATTGTSGATGCGCTGGCAGTGTTCCTGCGCCGGTTGCASTCGAT

TCCTGTST

SEQ ID NO 10
GBGCGAGBCGAAATACGCGATCGCTGTTAAAAGGACAATTACABACAGGAA

TCGABT

SEQ ID NO 11
TCGSCTCGCSCAGGCGCAATCACGAATGAATAACGGSTTGGTSGASG

SEQ ID NO 12
CSTGSTCBACBGGCCAGCCATTACGCTCGTCATCAAAATCACTCGCBTCBA

CCAABC

SEQ ID NO 13
SGTSGABCABGTCTGGAAAGAAATGCASAABCTSTTGCCBT

SEQ ID NO 14
BTCBAGSGAGAABTCACCATGAGTGACGACTGAATCCGGTGAGAASGGCAA

BAGSTTBT

SEQ ID NO 15
ASTTCTCBCTSGASAACCTTATTTTTGACGAGGGGAAATTAATAGGTTGTA

TTGASGTTGGACGBGT
```

-continued

SEQ ID NO 16
CBAGBTCCTGGTASCGGTCTGCGATTCCGACSCGTCCAACBTCA

SEQ ID NO 17
BTACCAGGASCTSGCCATCCTATGGAACTGCCTCGGTGAGTTTTCTCCSTC

BTTACAGAABC

SEQ ID NO 18
STTBTTCATBTCBGGATTATCAATACCATATTTTTGAAAAAGCCGSTTCTG

TAASGABG

SEQ ID NO 19
CSGASATGAASAABTTGCAGTTTCATTTGATGCTCGATGAGTTTTCTAAC

AGGATCCGCBCGBCSAG

SEQ ID NO 20
CTAGSGGSCGBTCSGTCCGTCCTGTCAGCTGCTBGSCGSGCG

The sequence for the protein that encodes kanamycin resistance was obtained from the literature. Using a software tool designed for this purpose, a gene that encodes the protein was broken down to 20 single stranded oligonucleotide fragments containing S (5-methyl-2'-deoxyisocytidine) and B (2'-deoxyisoguanosine) nucleotides at their 5' and 3' ends, ranging in size from 41 to 67 nucleotides (nts) (Table 1). These were the DNA oligonucleotide "fragments" with pre-selected sequences that, with partial overlap, would self-assemble in hybridization including S:B pairs, as the first step in the anneal-extend-ligate process.

Additionally, the LS-DNA product was designed to have a CACC tetranucleotide immediately upstream from the start codon; this assisted cloning into a TOPO expression vector. It was also designed to have a Bam HI region downstream of the stop codon. The complete designed sequence that is the intended product from the process of the instant invention was therefore 863 nts (Table 2).

Annealing, Extending and Ligating the Preselected DNA Oligonucleotide Fragments

The "anneal-extend-ligate" procedure was then executed with these 20 fragments, prepared by solid phase phosphoramidite synthesis. The procedure followed two different methods (AEL #1 and AEL #2). In each case, DNA (125-250 ng or each fragment) was used. Working stocks of 10 µM dNTPs were mixed with 5×ISO buffer and water to a final volume of 40 µL (one µL each oligo, 8 µL 5×ISO buffer, 12 µL water) in duplicate, and heated with the fragments, and then slowly cooled. Incubation programs were:

AEL #1: 95° C. for 5 minutes, temperature reduced at 0.1° C./second to 45° C.

AEL #2: 75° C. for 20 minutes, temperature reduced at 0.1° C./second to 60° C., held 30 minutes, temperature reduced 0.1° C./second to 4° C.

Aliquots (5 µL) of each annealing mixture were transferred to a new tube to which was added enzyme mixture containing polymerases, ligases, and substrates (15 µL). The mixtures were then incubated at 48° C. for 60 minutes to permit primer extension (using a non-strand displacing polymerase active at this temperature, preferably Phusion) in a procedure resembling that of [Gibson 2011]. The samples were then cooled and stored at 4° C. until PCR amplified.

PCR Amplification with Conversion of the Ligated LS-DNA Product

PCR reactions set up with 1 µL assembly mixture and either no added disoGTP (dBTP) or 0.5 µL added dBTP. The forward and reverse primers were:

KanR For: CACCATGAGCCATATTCAACGG SEQ ID NO 21

KanR Rev: GTCCGTCCTGTCAGCTGC SEQ ID NO 22

As the reverse primer was designed to be upstream of the final AEGIS nucleotides, the final PCR product was 849 bp. The PCR cycling program was: 95° C. 2 minutes, followed by 30 cycles of 95° C. 40 seconds, 55° C. 20 seconds, 72° C. 2 minutes, with a final extension of 72° C. 15 minutes.

TABLE 2

| PCR Recipe | | |
|---|---|---|
| Item | Per rxn | MMix (×6) |
| Taq Buffer, 10X | 5 µL | 30 µL |
| dNTP (10 mM) | 1 µL | 6 µL |
| KanR For (10 µM) | 2 µL | 12 µL |
| KanR Rev (10 µM) | 2 µL | 12 µL |
| Taq polymerase | 0.4 µL | 2.4 µL |
| DNA or water | 1 µL | — |
| Water | 38.6 µL | 231.6 µL |
| dBTP (10 mM) | 0.3 or 0 µL | — |

Two methods were used for the PCR amplification (with conversion) of the annealed, extended, and ligated construct. In the second, 2'-deoxyisoguanosine triphosphate (dBTP) is present in small amounts; in the first, it is absent. Gel electrophoretic analysis of the products showed the largest at the expected length of 863 bp. Ladder bands were observed, and presumed to represent incomplete assemblies. The same ladder structure is evident for both incubation methods, and both methods resulted in strong doublet products as the top of the gel.

The second method (where dBTP is present) appears to give more of the desired product, and is presently preferred. While not wishing to be bound by theory, we interpret this result as evidence that the presence of dBTP facilitates the copying of templates containing dS.

The PCR product was then ligated into a TOPO expression vector. This was used to transform Top10 cells by electroporation. Transformed cells were grown in the presence of kanamycin, harvested, and the plasmid recovered, and a sampling of the recovered plasmids was sequenced. The sequences (Table 2) showed essentially no error in the annealing, extension, ligation, or conversion steps; they did show errors common in sequences at the ends of long reads.

To show that the LS-DNA was functional, E. coli cells containing it were plated on LB/agar containing kanamycin (100 µg/mL) and IPTG (0.1 mm) from cultures prepared from BL21(DE3) cells transformed with pET TOPO expression vector containing the insert encoding for the kanamycin resistance protein. A negative control plate was spread with a culture of cells containing vector but no insert, a fact confirmed with PCR using vector primers.

TABLE 2

```
5 Sequences of gene for kanamycin resistance. AEGIS bases are highlighted

KanR_AEGIS       CTAGTGGSCGBTCTGSCCGTCCTGTCAGCTGCTBGSCGSGCGGATCCTGT  SEQ ID NO 23
KanR_normal      ------------------------------------------------T  SEQ ID NO 24
Kan09 with dBTP  --------------GTCCGACCTGTCAGCTGCTAGTCGTGCGGATCCTGT  SEQ ID NO 25
```

TABLE 2-continued

5 Sequences of gene for kanamycin resistance. AEGIS bases are highlighted

| | | |
|---|---|---|
| Kan11 with dBTP    | ---------------GTCCGTCCTGTCAGCTGCTAGTCGTGCGGATCCCGT | SEQ ID NO 26 |
| Kan14 with dBTP    | -------------------GTCCTGCCAGCTGCTATTCGGGGGGATCCTGT | SEQ ID NO 27 |
| Kan12 without dBTP | ---------------GTCCGTCCTGTCAGCTGCTAGTCGTGCGGATCCTGT | SEQ ID NO 28 |
| Kan13 without dBTP | ---------------GTCCGTCCTGTCAGCTGCTAGTCGTGCGGATCCTGT | SEQ ID NO 29 |
| | | |
| KanR_AEGIS         | TAGAAAAACTCATCGAGCATCAAATGAAACTGCAASTTBTTCATBTCBGG  | SEQ ID NO 23 |
| KanR_normal        | TAGAAAAACTCATCGAGCATCAAATGAAACTGCAATTTATTCATATCAGG  | SEQ ID NO 24 |
| Kan09 with dBTP    | CAGAAAAACTCATCGAGCATCAAATGAAACTGCAATTTGTTCATATCCGG  | SEQ ID NO 25 |
| Kan11 with dBTP    | TAGAAAAACTCATCGAGCATCAAATGAAACTGCAATTTATTCATATCAGG  | SEQ ID NO 26 |
| Kan14 with dBTP    | TAGATCC-TTCATCGAGCATCATATGAAACTGCAATTTATTCATATCAGG  | SEQ ID NO 27 |
| Kan12 without dBTP | TAGAAAAACTCATCGAGCATCAAATGAAACTGCAATTTATTCATATCAGG  | SEQ ID NO 28 |
| Kan13 without dBTP | TAGAAAAACTCATCGAGCATCAAATGAAACTGCAATTTATTCATATCAGG  | SEQ ID NO 29 |
| | | |
| KanR_AEGIS         | ATTATCAATACCATATTTTTGAAAAAGCCGSTTCTGTAASGABGGAGAAA  | SEQ ID NO 23 |
| KanR_normal        | ATTATCAATACCATATTTTTGAAAAAGCCGTTTCTGTAATGAAGGAGAAA  | SEQ ID NO 24 |
| Kan09 with dBTP    | ATTATCAATACCATATTTTTGAAAAAGCCGTTTCTGTAATGAAGGACAAA  | SEQ ID NO 25 |
| Kan11 with dBTP    | ATTATCAATACCATATTTTTGAAAAAGCCGTTTCTGTAATGAAGGAGAAA  | SEQ ID NO 26 |
| Kan14 with dBTP    | ATTATCAATACCATATTTTTGAAAAAGCTTTTTCTGCAATGACCGAAAAA  | SEQ ID NO 27 |
| Kan12 without dBTP | ATTATCAATACCATATTTTTGAAAAAGCCGTTTCTGTAATGAAGGAGAAA  | SEQ ID NO 28 |
| Kan13 without dBTP | ATTATCAATACCATATTTTTGAAAAAGCCGCTTCTGTAATGAAGGAGAAA  | SEQ ID NO 29 |
| | | |
| KanR_AEGIS         | ACTCACCGAGGCAGTTCCATAGGATGGCBAGBTCCTGGTASCGGTCTGCG  | SEQ ID NO 23 |
| KanR_normal        | ACTCACCGAGGCAGTTCCATAGGATGGCAAGATCCTGGTATCGGTCTGCG  | SEQ ID NO 24 |
| Kan09 with dBTP    | ACTCACCGAGGCAGTTCCATAGGATGGCAAGATCCTGGTATCGGTCTGCG  | SEQ ID NO 25 |
| Kan11 with dBTP    | ACTCACCGAGGCAGTTCCATAGGATGGCAAGATCCTGGTATCGGTCTGCG  | SEQ ID NO 26 |
| Kan14 with dBTP    | ACTCACCGAGGCAGTTCCATAGGATGGCAAGATCCTGGTATCGGTCTGCG  | SEQ ID NO 27 |
| Kan12 without dBTP | ACTCACCGAGGCAGTTCCATAGGATGGCAAGATCCTGGTATCGGTCTGCG  | SEQ ID NO 28 |
| Kan13 without dBTP | ACTCACCGAGGCAGTTCCATAGGATGGCAAGATCCTGGTATCGGTCTGCG  | SEQ ID NO 29 |
| | | |
| KanR_AEGIS         | ATTCCGACSCGSCCBACBTCAATACAACCTATTAATTTCCCCTCGTCAAA  | SEQ ID NO 23 |
| KanR_normal        | ATTCCGACTCGTCCAACATCAATACAACCTATTAATTTCCCCTCGTCAAA  | SEQ ID NO 24 |
| Kan09 with dBTP    | ATTCCGACTCGTCCAACATCAATACAACCTATTAATTTCCCCTCGTCAAA  | SEQ ID NO 25 |
| Kan11 with dBTP    | ATTCCGACTCGTCCAACATCAATACAACCTATTAATTTCCCCTCGTCAAA  | SEQ ID NO 26 |
| Kan14 with dBTP    | ATTCCGACTCGTCCAACATCAATACAACCTATTA-TTTCCCCTCGTCAAA  | SEQ ID NO 27 |
| Kan12 without dBTP | ATTCCGACTCGTCCAACATCAATACAACCTATTAATTTCCCCTCGTCAAA  | SEQ ID NO 28 |
| Kan13 without dBTP | ATTCCGACTCGTCCAACATCAATACAACCTATTAATTTCCCCTCGTCAAA  | SEQ ID NO 29 |
| | | |
| KanR_AEGIS         | AATAAGGTTBTCBAGSGAGAABTCACCATGAGTGACGACTGAATCCGGTG  | SEQ ID NO 23 |
| KanR_normal        | AATAAGGTTATCAAGTGAGAAATCACCATGAGTGACGACTGAATCCGGTG  | SEQ ID NO 24 |
| Kan09 with dBTP    | AATAAGGTTATCAAGTGAGAAATCACCATGAGTGACGACTGAATCCGGTG  | SEQ ID NO 25 |
| Kan11 with dBTP    | AATAAGGTTATCAAGTGAGAAATCACCATGAGTGACGACTGAATCCGGTG  | SEQ ID NO 26 |
| Kan14 with dBTP    | AATAAGGTTATCAAGAGAGAAATCTCCATGAGTGACGACTGAATTTTGTA  | SEQ ID NO 27 |
| Kan12 without dBTP | AATAAGGTTATCAAGTGAGAAATCACCATGAGTGACGACTGAATCCGGTG  | SEQ ID NO 28 |
| Kan13 without dBTP | AATAAGGTTATCAAGTGAGAAATCACCATGAGTGACGACTGAATCCGGTG  | SEQ ID NO 29 |
| | | |
| KanR_AEGIS         | AGAASGGCAABAGSTTBTGCATTTCTTTCCAGACSTGSTCBACBGGCCAG  | SEQ ID NO 23 |
| KanR_normal        | AGAATGGCAAAAGTTTATGCATTTCTTTCCAGACTTGTTCAACAGGCCAG  | SEQ ID NO 24 |
| Kan09 with dBTP    | AGAATGGCAAAAGTTTATGCATTTCTTTCCAGACTTGTTCAACAGGCCAG  | SEQ ID NO 25 |
| Kan11 with dBTP    | AGAATGGCAAAAGTTTATGCATTTCTTTCCAGACTTGTTCAACAGGCCAG  | SEQ ID NO 26 |
| Kan14 with dBTP    | AGAATGGCAAAAGTTTATGCATTTCTTTCCAGACTTGATCAACAGGCCAG  | SEQ ID NO 27 |
| Kan12 without dBTP | AGAATGGCAAAAGTTTATGCATTTCTTTCCAGACTTGTTCAACAGGCCAG  | SEQ ID NO 28 |
| Kan13 without dBTP | AGAATGGCAAAAGTTTATGCATTTCTTTCCAGACTTGTTCAACAGGCCAG  | SEQ ID NO 29 |
| | | |
| KanR_AEGIS         | CCATTACGCTCGTCATCAAAATCACTCGCBTCBACCAABCCGTTATTCAT  | SEQ ID NO 23 |
| KanR_normal        | CCATTACGCTCGTCATCAAAATCACTCGCATCAACCAACCGTTATTCAT   | SEQ ID NO 24 |
| Kan09 with dBTP    | CCATTACGCTCGTCATCAAAATCACTCGCATCAACCAACCCGTTATTCAT  | SEQ ID NO 25 |
| Kan11 with dBTP    | CCATTACGCTCGTCATCAAAATCACTCGCATCAACCAAACCGTTATTCAT  | SEQ ID NO 26 |
| Kan14 with dBTP    | CCATTACGOTCGTCATCAAAATCACTCGCATCAACCAACCCGTTATTCAT  | SEQ ID NO 27 |
| Kan12 without dBTP | CCATTACGCTCGTCATCAAAATCACTCGCATCAACCAAACCGTTATTCAT  | SEQ ID NO 28 |
| Kan13 without dBTP | CCATTACGCTCGTCATCAAAATCACTCGCATCCACCAAACCGTTATTCAT  | SEQ ID NO 29 |
| | | |
| KanR_AEGIS         | TCGTGATTGCGCCTGBGCGAGBCGAAATACGCGATCGCTGTTAAAAGGAC  | SEQ ID NO 23 |
| KanR_normal        | TCGTGATTGCGCCTGAGCGAGACGAAATACGCGATCGCTGTTAAAAGGAC  | SEQ ID NO 24 |
| Kan09 with dBTP    | TCGTGATTGCGCCTGAGCGAGACGAAATACGCGATCGCTGTTAAAAGGAC  | SEQ ID NO 25 |
| Kan11 with dBTP    | TCGTGATTGCGCCCGAGCGAGACGAAATACGCGATCGCTGTTAAAAGGAC  | SEQ ID NO 26 |
| Kan14 with dBTP    | TCGTGATTGCGCCTGAGCGAGACGAAATACGCGATCGCTGTTAAAAGGAC  | SEQ ID NO 27 |
| Kan12 without dBTP | TCGTGATTGCGCCTGAGCGAGACGAAATACGCGATCGCTGTTAAAAGGAC  | SEQ ID NO 28 |
| Kan13 without dBTP | TCGTGATTGCGCCTGAGCGAGACGAAATACGCGATCGCTGTTAAAAGGAC  | SEQ ID NO 29 |
| | | |
| KanR_AEGIS         | AATTACBAACBGGAATCGABTGCAACCGGCGCAGGAACACTGCCAGCGCA  | SEQ ID NO 23 |
| KanR_normal        | AATTACAAACAGGAATCGAATGCAACCGGCGCAGGAACACTGCCAGCGCA  | SEQ ID NO 24 |
| Kan09 with dBTP    | AATTACAAACAGGAATCGAATGCAACCGGCGCAGGAACACTGCCAGCGCA  | SEQ ID NO 25 |
| Kan11 with dBTP    | AATTACAAACAGGAATCGAATGCAACCGGCGCAGGAACACTGCCAGCGCA  | SEQ ID NO 26 |
| Kan14 with dBTP    | AATTACAAACAGGAATCGAATGCAACCGGCGCAGGAACACTGCCAGCGCA  | SEQ ID NO 27 |
| Kan12 without dBTP | AATTACAAACAGGAATCGAATGCAACCGGCGCAGGAACACTGCCAGCGCA  | SEQ ID NO 28 |
| Kan13 without dBTP | AATTACAAACAGGAATCGAATGCAACCGGCGCAGGAACACTGCCAGCGCA  | SEQ ID NO 29 |

TABLE 2-continued

5 Sequences of gene for kanamycin resistance. AEGIS bases are highlighted

```
KanR_AEGIS          TCBACAATBTTSTCBCCTGAATCAGGATATTCTTCTAATACCTGGAASGC SEQ ID NO 23
KanR_normal         TCAACAATATTTTCACCTGAATCAGGATATTCTTCTAATACCTGGAATGC SEQ ID NO 24
Kan09 with dBTP     TCAACAATATTTTCACCTGAATCAGGATATTCTTCTAATACCTGGAATGC SEQ ID NO 25
Kan11 with dBTP     TCAACAATATTTTCACCTGAATCAGGATATTCTTCTAATACCTGGAATGC SEQ ID NO 26
Kan14 with dBTP     TCAACAATATTTTCACCTGAATCAGGATATTCTTCTAATACCTGGAATGC SEQ ID NO 27
Kan12 without dBTP  TCAACAATATTTTCACCTGAATCAGGATATTCTTCTAATACCTGGAATGC SEQ ID NO 28
Kan13 without dBTP  TCAACAATATTTTCACCTGAATCAGGATATTCTTCTAATACCTGGAATGC SEQ ID NO 29

KanR_AEGIS          SGTSTTSCCGGGGATCGCAGTGGTGAGTAACCATGCATCBTCBGGBGTBC SEQ ID NO 23
KanR_normal         TGTTTTTCCGGGGATCGCAGTGGTGAGTAACCATGCATCATCAGGAGTAC SEQ ID NO 24
Kan09 with dBTP     TGTTTTTCCGGGGATCGCAGTGGTGAGTAACCATGCATCATCAGGAGTAC SEQ ID NO 25
Kan11 with dBTP     TGTTTTTCCGGGGATCGCAGTGGTGAGTAACCATGCATCATCAGGAGTAC SEQ ID NO 26
Kan14 with dBTP     TGTTTTTCCGGGGATCGCAGTGGTGAGTAACCATGCATCATCAGGAGTAC SEQ ID NO 27
Kan12 without dBTP  TGTTTTTCCGGGGATCGCAGTGGTGAGTAACCATGCATCATCAGGAGTAC SEQ ID NO 28
Kan13 without dBTP  TGTTTTTCCGGGGATCGCAGTGGTGAGTAACCATGCATCATCAGGAGTAC SEQ ID NO 29

KanR_AEGIS          GGATAAAATGCTTGATGGTCGGBAGBGGCATAAA-STCCGTCAGCCAGTT SEQ ID NO 23
KanR_normal         GGATAAAATGCTTGATGGTCGGAAGAGGCATAAA-TTCCGTCAGCCAGTT SEQ ID NO 24
Kan09 with dBTP     GGATAAAATGCTTGATGGTCGGAAGAGGCATAAA-TTCCGTCAGCCAGTT SEQ ID NO 25
Kan11 with dBTP     GGATAAAATGCTTGATGGTCGGAAGAGGCATAAA-TTCCGTCAGCCAGTT SEQ ID NO 26
Kan14 with dETP     GGATAAAATGCTTGATGGTCGGAAGAGGCATAAA-TTCCGTCAGCCAGTT SEQ ID NO 27
Kan12 without dBTP  GGATAAAATGCTTGATGGTCGGAAGAGGCATAAAGTCCGTCAGCCAGTT  SEQ ID NO 28
Kan13 without dBTP  GGATAAAATGCTTGATGGTCGGAAGAGGCATAAA-TTCCGTCAGCCAGTT SEQ ID NO 29

KanR_AEGIS          TAGTCTGACCATCTCATCTGTBACBTCBTTGGCABCGCT-ACCTTTGCCA SEQ ID NO 23
KanR_normal         TAGTCTGACCATCTCATCTGTAACATCATTGGCAACGCT-ACCTTTGCCA SEQ ID NO 24
Kan09 with dBTP     TAGTCTGACCATCTCATCTGTAACATCATTGGCAACGCT-ACCTTTGCCA SEQ ID NO 25
Kan11 with dBTP     TAGTCTGACCATCTCATCTGTCACATCATTGGCAACGCT-ACCTTTGCCA SEQ ID NO 26
Kan14 with dBTP     TAGTCTGACCATCTCATCTGTAACATCATTGGCCACGCT-ACCTTTGCCA SEQ ID NO 27
Kan12 without dBTP  TAGTCTGACCATCTCATCTGTAACATCATTGGCAACGCTTACCTTTGCCA SEQ ID NO 28
Kan13 without dBTP  TAGTCTGACCATCTCATCTGTAACATCATTGGCAACGCT-ACCTTTGCCA SEQ ID NO 29

KanR_AEGIS          TGTTT-CAGAAACAACTCS-GGCGCBTCGGG-CTTCCCA-TACAAGCGAT SEQ ID NO 23
KanR_normal         TGTTT-CAGAAACAACTCT-GGCGCATCGGG-CTTCCCA-TACAAGCGAT SEQ ID NO 24
Kan09 with dBTP     TGTTT-CAGAAACAACTCG-GGCGCATCGGG-CTTCCCA-TACAAGCGAT SEQ ID NO 25
Kan11 with dBTP     TGTTT-CAGAAACAACTCT-GGCGCATCGGG-CTTCCCA-TACAAGCGAT SEQ ID NO 26
Kan14 with dBTP     TGTTT-CAGAAACAACTCT-GGCGCATCGGG-CTTCCCA-TACAAGCGAT SEQ ID NO 27
Kan12 without dBTP  TGTTTTCAGAAACAACTCT-GGCGCATCGGG-CTTCCCAATACAAGCGAT SEQ ID NO 28
Kan13 without dBTP  TGTTT-CAGAAACAACTCTTGGCGCATCGGGGCTTCCCCATACAAGCGAT SEQ ID NO 29

KanR_AEGIS          A-GATT-GTC-GCACCS-GASTGCCC-GACBTT-ATCGCG--AGCCCATT SEQ ID NO 23
KanR_nomal          A-GATT-GTC-GCACCT-GATTGCCC-GACATT-ATCGCG--AGCCCATT SEQ ID NO 24
Kan09 with dBTP     A-GATT-GTC-GCACCT-GATTGCCC-GACATT-ATCGCG--AGCCCATT SEQ ID NO 25
Kan11 with dBTP     A-GATT-GTC-GCACCT-GATTGCCC-GACATT-ATCGCA--AGCCCATT SEQ ID NO 26
Kan14 with dBTP     A-GATT-GTC-GCACCT-GATTGCCC-GACATT-ATCGCG--AGCCCATT SEQ ID NO 27
Kan12 without dBTP  ATGATT-GTCCGCACCC-GAGTGCCCCGACATTTATCGCGGAGGCCCATT SEQ ID NO 28
Kan13 without dBTP  TAGATTTGTC-GCACCCTGATTGCCCCGACCTTTATCGCG--AGCCCATT KanR_AEGIS          T-ATACCCAT-ATAAB-TCBGCBTCC-ATGTT--GGAATTTAAT-CG--C SEQ ID NO 23
KanR_normal         T-ATACCCAT-ATAAA-TCAGCATCC-ATGTT--GGAATTTAAT-CG--C SEQ ID NO 24
Kan09 with dBTP     T-ATACCCAT-ATAAA-TCAGCATCC-ATGTT--GGAATTTAAT-CG--C SEQ ID NO 25
Kan11 with dBTP     T-ATACCCAT-ATAAA-TCAGCCTCC-ATGTT--GGAATTTAAT-CG--C SEQ ID NO 26
Kan14 with dBTP     T-ATACCCAT-ATAAA-TCAGCATCC-ATGTT--GGAATTTAAT-CG--C SEQ ID NO 27
Kan12 without dBTP  TTATACCCATTATAAAATCACCATCCCATGTTTGGGAATTTAAT-CGGCG SEQ ID NO 28
Kan13 without dBTP  TTATACCCAT-ATAAA-TCAGCATCC-ATGTT-GGAAATTTAATTCG--C SEQ ID NO 29

KanR_AEGIS          GGCCTC-GACGTTTCCC--GTTGAATATGGCTCATGGTG-- 863 SEQ ID NO 23
KanR_normal         GGCCTC-GACGTTTCCC--GTTGAATATGGCTCAT------ 810 SEQ ID NO 24
Kan09 with dBTP     GGCCTC-GACGTTTCCC--GTTGAATATGGCTCATGGTG-- 849 SEQ ID NO 25
Kan11 with dBTP     GGCCTC-GACGTTTCCC--GTTGAATATGGCTCATGGTG-- 849 SEQ ID NO 26
Kan14 with dBTP     GGCCTC-GACGTTTCCC--GTTGAATATGGCTCATGGTG-- 843 SEQ ID NO 27
Kan12 without dBTP  GGCCTCCAACGTTTCCCCGGTTGAATATGGCTTCTAGGGTG 872 SEQ ID NO 28
Kan13 without dBTP  GGCCTCCGACGTTTTCCC-GTTGAATATGGCTCATGGGA-- 862 SEQ ID NO 29
```

What is claimed is:

1. A process for creating a double stranded DNA ligated product having a preselected sequence, said process comprising:

(a) annealing a set of single stranded DNA oligonucleotides having preselected sequences, wherein one or more of said oligonucleotides contain at least two nonstandard nucleotides that implement one or more nonstandard hydrogen bonding patterns in segments that hybridize to segments of another of said oligonucleotides that contain at least two complementary non-standard nucleotides that implement one or more non-standard hydrogen bonding patterns, (b) extending the annealed oligonucleotides hybridized at their 3'-ends strand by incubating with 2'-deoxynucleoside triphosphates and a DNA polymerase that is not strand-displacing, and (c) ligating the extended strands with a ligase.

2. The process of claim 1, wherein said process comprises an additional step, said additional step comprising contacting said ligated product with 2'-deoxynucleoside triphosphates and a DNA polymerase that incorporates standard nucleotides opposite said non-standard nucleotides, copying the strands of said ligated product two or more cycles, and obtaining a product wherein said non-standard nucleotides that implement one or more non-standard hydrogen bonding patterns are replaced by standard nucleotides.

3. The process of claim 1, wherein said non-standard nucleotides comprise heterocycles selected from the group consisting of

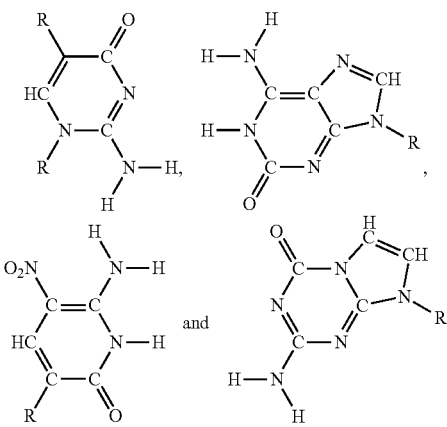

wherein R is the point of attachment between the heterocycles to the said DNA oligonucleotides.

4. The process of claim 2, wherein said non-standard nucleotides comprise heterocycles selected from the group consisting of

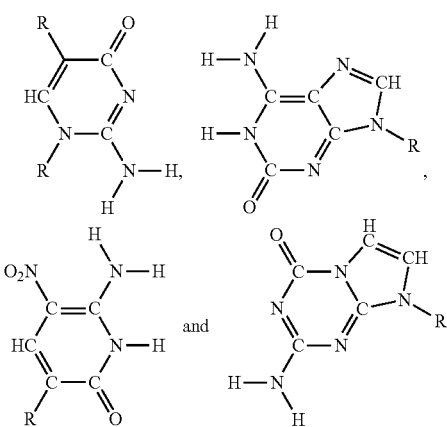

wherein R is the point of attachment between the heterocycles to the said DNA oligonucleotides.

5. The process of claim 1, wherein said polymerase is Phusion.

6. The process of claim 2, wherein said process replaces the heterocycle

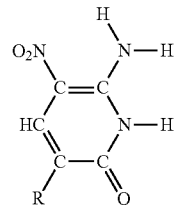

by the heterocycle cytosine, wherein R is the point of attachment between the heterocycles to the said DNA oligonucleotides.

7. The process of claim 2, wherein said process replaces the heterocycle

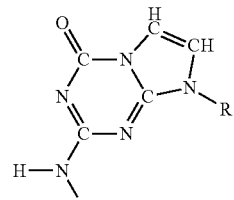

by the heterocycle guanine, wherein R is the point of attachment between the heterocycles to the said DNA oligonucleotides.

8. The process of claim 2, wherein said process replaces the heterocycle

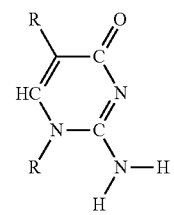

by the heterocycle thymine, wherein R is the point of attachment between the heterocycles to the said DNA oligonucleotides.

9. The process of claim 2, wherein said process replaces the heterocycle

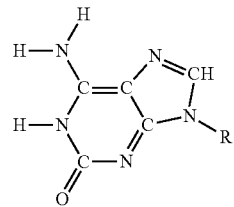

by the heterocycle adenine, wherein R is the point of attachment between the heterocycles to the said DNA oligonucleotides.

* * * * *